(12) United States Patent
Yang

(10) Patent No.: US 11,077,322 B2
(45) Date of Patent: Aug. 3, 2021

(54) SYSTEMS AND METHODS FOR CALIBRATING RADIATION DEVICE

(71) Applicant: SHANGHAI UNITED IMAGING HEALTHCARE CO., LTD., Shanghai (CN)

(72) Inventor: Hongcheng Yang, Shanghai (CN)

(73) Assignee: SHANGHAI UNITED IMAGING HEALTHCARE CO. LTD., Shanghai (CN)

( * ) Notice: Subject to any disclaimer, the term of this patent is extended or adjusted under 35 U.S.C. 154(b) by 41 days.

(21) Appl. No.: 16/565,632

(22) Filed: Sep. 10, 2019

(65) Prior Publication Data

US 2020/0078605 A1 Mar. 12, 2020

(30) Foreign Application Priority Data

Sep. 12, 2018 (CN) .......................... 201811063410.5
Jun. 24, 2019 (CN) .......................... 201910547282.X

(51) Int. Cl.
*A61N 5/10* (2006.01)

(52) U.S. Cl.
CPC .......... *A61N 5/1075* (2013.01); *A61N 5/1045* (2013.01); *A61N 5/1049* (2013.01); *A61N 5/1067* (2013.01); *A61N 2005/1054* (2013.01); *A61N 2005/1074* (2013.01)

(58) Field of Classification Search
None
See application file for complete search history.

(56) References Cited

U.S. PATENT DOCUMENTS

| 2006/0122502 A1 | 6/2006 | Scherch et al. |
| 2009/0067576 A1 | 3/2009 | Maltz |
| 2017/0318651 A1 | 11/2017 | Canfield et al. |
| 2018/0272155 A1 * | 9/2018 | Thieme ................ A61B 6/5258 |
| 2020/0289080 A1 | 9/2020 | Yang et al. |

FOREIGN PATENT DOCUMENTS

CN 106650700 A 5/2017

OTHER PUBLICATIONS

First Office Action in Chinese Application No. 201910547282.X dated Aug. 5, 2020, 36 pages.

* cited by examiner

*Primary Examiner* — Hoon K Song
(74) *Attorney, Agent, or Firm* — Metis IP LLC

(57) ABSTRACT

The present disclosure is related to systems and methods for calibrating a radiation device. The method includes obtaining a plurality of images acquired at each of at least one source-to-image distance (SID) by the imaging device. The method includes determining, based on the plurality of images, at least one first projection position of a first axis of the collimator on the imaging device and at least one second projection position of a second axis of the radiation beam on the imaging device. The method includes determining, based on the at least one first projection position and the at least one second projection position, at least one offset distance between the first projection position and the second projection position. The method includes determining whether to calibrate the radiation device by comparing the at least one offset distance with a threshold.

18 Claims, 13 Drawing Sheets

800

---

Determining, based on at least one first image acquired at a SID, a first projection position of a first axis of a collimator on an imaging device ⟶ 810

↓

Determining, based on at least one second image acquired at the SID, a second projection position of a second axis of a radiation beam on the imaging device ⟶ 820

↓

Determining, based on the first projection position of the first axis of the collimator on the imaging device and the second projection position of the second axis of the radiation beam on the imaging device, an offset distance associated with the SID ⟶ 830

FIG. 8

SYSTEMS AND METHODS FOR CALIBRATING RADIATION DEVICE

CROSS-REFERENCE TO RELATED APPLICATIONS

This application claims priority of Chinese Patent Application No. 201811063410.5, filed on Sep. 12, 2018, and Chinese Patent Application No. 201910547282.X, filed on Jun. 24, 2019, the contents of each of which are hereby incorporated by reference.

TECHNICAL FIELD

This disclosure generally relates to a radiation system, and more particularly, relates to systems and methods for calibrating a radiation device in the radiation system.

BACKGROUND

Radiotherapy has been widely used for clinical treatment of cancers and other conditions. A fundamental goal of the radiotherapy is to kill cells (usually tumor cells), suppress inflammation, suppress the immune system, or prevent tumor recurrence using high-energy radiation beams such as X-rays, gamma rays, alpha rays, beta rays, etc. One of a most challenging problems in a radiation treatment is to target radiation at a region of interest (ROI) precisely for treatment so as to reduce unnecessary radiation toward normal organs or tissues surrounding the ROI.

A treatment head of a radiation device is typically provided with a collimator for beam shaping to modify a shape of a radiation beam emitted from a radiation source to a desired shape of an ROI to be treated in a treatment plan. The collimator can be rotated around a rotation axis of the collimator to shape the radiation beam to generate any one of a plurality of suitable beam shapes. Generally, the radiation device needs to be adjusted, calibrated, and/or verificated to ensure that the rotation axis of the collimator is aligned with a beam axis of the radiation beam. However, current radiation device tuning, calibration and verification protocols are usually slow, inaccurate, involve external hardware (e.g., a water tank), and/or rely on subjective human decisions. Therefore, it is desirable to provide systems and methods for facilitating the calibration of a radiation device in a radiation system.

SUMMARY

According to an aspect of the present disclosure, a method for calibrating a radiation device may be implemented on a computing device having one or more processors and one or more storage devices. The radiation device may include a radiation source, a collimator, and a detector of an imaging device disposed opposite to the radiation source. The radiation source may be configured to emit a radiation beam. The collimator may be configured to block the radiation beam. The method may include obtaining a plurality of images acquired at each of at least one source-to-image distance (SID) by the imaging device. The method may include determining, based on the plurality of images, at least one first projection position of a first axis of the collimator on the imaging device and at least one second projection position of a second axis of the radiation beam on the imaging device. The method may include determining, based on the at least one first projection position and the at least one second projection position, at least one offset distance between the first projection position and the second projection position. The method may include determining whether to calibrate the radiation device by comparing the at least one offset distance with a threshold.

In some embodiments, the method may include calibrating the radiation device by adjusting at least one component of the radiation device.

In some embodiments, the plurality of images may include at least one first image and at least one second image. For each SID of the at least one SID, the method may include determining, based on the at least one first image acquired at the SID, the first projection position of the first axis of the collimator on the imaging device. The method may include determining, based on the at least one second image acquired at the SID, the second projection position of the second axis of the radiation beam on the imaging device.

In some embodiments, the method may include obtaining the at least one first image by rotating the collimator around the first axis of the collimator.

In some embodiments, the at least one first image may include a projection image of at least one of a marker board, a jaw, or a multi-leaf collimator.

In some embodiments, the method may include the at least one second image may include a projection image of the phantom.

In some embodiments, the method may include the imaging device may be an electronic portal imaging device (EPID).

According to another aspect of the present disclosure, a method for calibrating a radiation device may be implemented on a computing device having one or more processors and one or more storage devices. The radiation device may include a radiation source, a collimator, and a detector of an imaging device disposed opposite to the radiation source. The radiation source may be configured to emit a radiation beam. The collimator may be configured to adjust the radiation beam. The method may include obtaining a plurality of images acquired at each source-to-image distances (SID) of a plurality of SIDs by the imaging device. The method may include determining, based on the plurality of images, a first projection position of a first axis of the collimator on the imaging device associated with the each SID of the plurality of SIDs and a second projection position of a second axis of the radiation beam on the imaging device associated with the each SID of the plurality of SIDs. The method may include determining, based on the first projection position of the first axis of the collimator on the imaging device associated with the each SID of the plurality of SIDs and the second projection position of the second axis of the radiation beam on the imaging device associated with the each SID of the plurality of SIDs, an offset distance associated with the each SID of the plurality of SIDs. The method may include determining, based on the plurality of SIDs and the offset distance associated with the each SID of the plurality of SIDs, a deviation between the first axis of the collimator and the second axis of the radiation beam.

In some embodiments, the plurality of images may include at least one first image and at least one second image. For each SID of the plurality of SIDs, the method may include determining, based on the at least one first image acquired at the SID, the first projection position of the first axis of the collimator on the imaging device associated with the SID. The method may include determining, based on the at least one second image acquired at the SID, the second projection position of the second axis of the radiation beam on the imaging device associated with the SID.

In some embodiments, the method may include obtaining the at least one first image by rotating the collimator around the first axis of the collimator.

In some embodiments, the at least one first image may include a projection image of at least one of a marker board, a jaw, or a multi-leaf collimator.

In some embodiments, the at least one second image may include a projection image of the phantom.

In some embodiments, the deviation between the first axis of the collimator and the second axis of the radiation beam may include at least one of an angle of inclination of the first axis of the collimator relative to the second axis of the radiation beam, or an offset of the first axis of the collimator relative to the second axis of the radiation beam.

In some embodiments, the offset of the first axis of the collimator relative to the second axis of the radiation beam may include an offset distance between a first projection position of the first axis of the collimator and a second projection position of the second axis of the radiation beam on a target plane of the imaging device.

In some embodiments, the method may include determining, based on the plurality of SIDs, the plurality of offset distances, and a geometric relationship between the plurality of SIDs and the plurality of offset distances, at least one of an angle of inclination of the first axis of the collimator relative to the second axis of the radiation beam or an offset of the first axis of the collimator relative to the second axis of the radiation beam.

In some embodiments, the method may include determining, based on the plurality SIDs, the plurality of offset distances, and a geometric relationship between the plurality of SIDs and the plurality of offset distances, at least one of a plurality of initial angles of inclination of the first axis of the collimator relative to the second axis of the radiation beam or a plurality of initial offsets of the first axis of the collimator relative to the second axis of the radiation beam. The method may include determining, by performing a fitting operation based on at least one of the plurality of initial angles of inclination of the first axis of the collimator relative to the second axis of the radiation beam or the plurality of initial offsets of the first axis of the collimator relative to the second axis of the radiation beam, at least one of a target angle of inclination of the first axis of the collimator relative to the second axis of the radiation beam or a target offset of the first axis of the collimator relative to the second axis of the radiation beam.

In some embodiments, the method may include determining whether to calibrate the radiation device by comparing the deviation between the first axis of the collimator and the second axis of the radiation beam with a threshold.

In some embodiments, the method may include calibrating the radiation device by adjusting at least one component of the radiation device.

In some embodiments, the imaging device may be an electronic portal imaging device (EPID).

According to an aspect of the present disclosure, a method for calibrating a radiation device may be implemented on a computing device having one or more processors and one or more storage devices. The radiation device may include a radiation source, a collimator, and a detector of an imaging device disposed opposite to the radiation source. The radiation source may be configured to emit a radiation beam. The collimator may be configured to block the radiation beam. The method may include obtaining at least one first image acquired at a first source-to-image distance (SID) by the imaging device. The method may include obtaining at least one second image acquired at a second SID by the imaging device. The method may include determining at least one projection position of a first axis of the collimator on the imaging device based on the at least one first image and the at least one second image, the at least one projection position of the first axis of the collimator on the imaging device may include a first projection position of the first axis of the collimator on the imaging device when the imaging device is positioned to acquire the at least one first image at the first SID, and a second projection position of the first axis of the collimator on the imaging device when the imaging device is positioned to acquire the at least one second image at the second SID. The method may include obtaining at least one third image acquired at the first SID by the imaging device. The method may include obtaining at least one fourth image acquired at the second SID by the imaging device. The method may include determining at least one projection position of a second axis of the radiation beam on the imaging device based on the at least one third image and the at least one fourth image, the at least one projection position of the second axis of the radiation beam on the imaging device may include a third projection position of the second axis of the radiation beam on the imaging device when the imaging device is positioned to acquire the at least one third image at the first SID, and a fourth projection position of the second axis of the radiation beam on the imaging device when the imaging device is positioned to acquire the at least one fourth image at the second SID. The method may include determining, based on the at least one first image and the at least one third image, a first offset distance between the first projection position and the third projection position. The method may include determining, based on the at least one second image and the at least one fourth image, a second offset distance between the second projection position and the fourth projection position. The method may include determining, based on the first offset distance, the second offset distance, the first SID, and the second SID, a deviation between the first axis of the collimator and the second axis of the radiation beam.

In some embodiments, the method may include determining, based on the at least one first image, the first projection position. The method may include determining, based on the at least one second image, the second projection position.

In some embodiments, the method may include determining, based on the at least one third image, the third projection position. The method may include determining, based on the at least one fourth image, the fourth projection position.

In some embodiments, the method may include obtaining the at least one first image or the at least one second image by rotating the collimator around the first axis of the collimator.

In some embodiments, the at least one first image or the at least one second image may include a projection image of at least one of a marker board, a jaw, or a multi-leaf collimator.

In some embodiments, the at least one second image or the at least one fourth image may include a projection image of the phantom.

In some embodiments, the deviation between the first axis of the collimator and the second axis of the radiation beam may include at least one of an angle of inclination of the first axis of the collimator relative to the second axis of the radiation beam, or an offset of the first axis of the collimator relative to the second axis of the radiation beam.

In some embodiments, the offset of the first axis of the collimator relative to the second axis of the radiation beam may include an offset distance between a projection position of the first axis of the collimator and a projection position of the second axis of the radiation beam on a target plane of the imaging device.

In some embodiments, the method may include determining whether to calibrate the radiation device by comparing the deviation between the first axis of the collimator and the second axis of the radiation beam with a threshold.

In some embodiments, the method may include calibrating the radiation device by adjusting at least one component of the radiation device.

According to another aspect of the present disclosure, a system may include a radiation device, at least one storage medium storing a set of instructions, and at least one processor in communication with the at least one storage medium. The radiation device may include a radiation source, a collimator, and a detector of an imaging device disposed opposite to the radiation source. The radiation source may be configured to emit a radiation beam. The collimator may be configured to block the radiation beam. When executing the stored set of instructions, the at least one processor causes the system to perform a method. The method may include obtaining a plurality of images acquired at each of at least one source-to-image distance (SID) by the imaging device. The method may include determining, based on the plurality of images, at least one first projection position of a first axis of the collimator on the imaging device and at least one second projection position of a second axis of the radiation beam on the imaging device. The method may include determining, based on the at least one first projection position and the at least one second projection position, at least one offset distance between the first projection position and the second projection position. The method may include determining whether to calibrate the radiation device by comparing the at least one offset distance with a threshold.

According to another aspect of the present disclosure, a system may include a radiation device, at least one storage medium storing a set of instructions, and at least one processor in communication with the at least one storage medium. The radiation device may include a radiation source, a collimator, and a detector of an imaging device disposed opposite to the radiation source. The radiation source may be configured to emit a radiation beam. The collimator may be configured to block the radiation beam. When executing the stored set of instructions, the at least one processor causes the system to perform a method. The method may include obtaining a plurality of images acquired at each source-to-image distances (SID) of a plurality of SIDs by the imaging device. The method may include determining, based on the plurality of images, a first projection position of a first axis of the collimator on the imaging device associated with the each SID of the plurality of SIDs and a second projection position of a second axis of the radiation beam on the imaging device associated with the each SID of the plurality of SIDs. The method may include determining, based on the first projection position of the first axis of the collimator on the imaging device associated with the each SID of the plurality of SIDs and the second projection position of the second axis of the radiation beam on the imaging device associated with the each SID of the plurality of SIDs, an offset distance associated with the each SID of the plurality of SIDs. The method may include determining, based on the plurality of SIDs and the offset distance associated with the each SID of the plurality of SIDs, a deviation between the first axis of the collimator and the second axis of the radiation beam.

According to another aspect of the present disclosure, a system may include a radiation device, at least one storage medium storing a set of instructions, and at least one processor in communication with the at least one storage medium. The radiation device may include a radiation source, a collimator, and a detector of an imaging device disposed opposite to the radiation source. The radiation source may be configured to emit a radiation beam. The collimator may be configured to block the radiation beam. When executing the stored set of instructions, the at least one processor causes the system to perform a method. The method may include obtaining at least one first image acquired at a first source-to-image distance (SID) by the imaging device. The method may include obtaining at least one second image acquired at a second SID by the imaging device. The method may include determining at least one projection position of a first axis of the collimator on the imaging device based on the at least one first image and the at least one second image, the at least one projection position of the first axis of the collimator on the imaging device may include a first projection position of the first axis of the collimator on the imaging device when the imaging device is positioned to acquire the at least one first image at the first SID, and a second projection position of the first axis of the collimator on the imaging device when the imaging device is positioned to acquire the at least one second image at the second SID. The method may include obtaining at least one third image acquired at the first SID by the imaging device. The method may include obtaining at least one fourth image acquired at the second SID by the imaging device. The method may include determining at least one projection position of a second axis of the radiation beam on the imaging device based on the at least one third image and the at least one fourth image, the at least one projection position of the second axis of the radiation beam on the imaging device may include a third projection position of the second axis of the radiation beam on the imaging device when the imaging device is positioned to acquire the at least one third image at the first SID, and a fourth projection position of the second axis of the radiation beam on the imaging device when the imaging device is positioned to acquire the at least one fourth image at the second SID. The method may include determining, based on the at least one first image and the at least one third image, a first offset distance between the first projection position and the third projection position. The method may include determining, based on the at least one second image and the at least one fourth image, a second offset distance between the second projection position and the fourth projection position. The method may include determining, based on the first offset distance, the second offset distance, the first SID, and the second SID, a deviation between the first axis of the collimator and the second axis of the radiation beam.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein:

FIG. 8 is a flowchart illustrating an exemplary process for determining an offset distance associated with a source-to-image distance (SID) according to some embodiments of the present disclosure;

DETAILED DESCRIPTION

Figure 1:
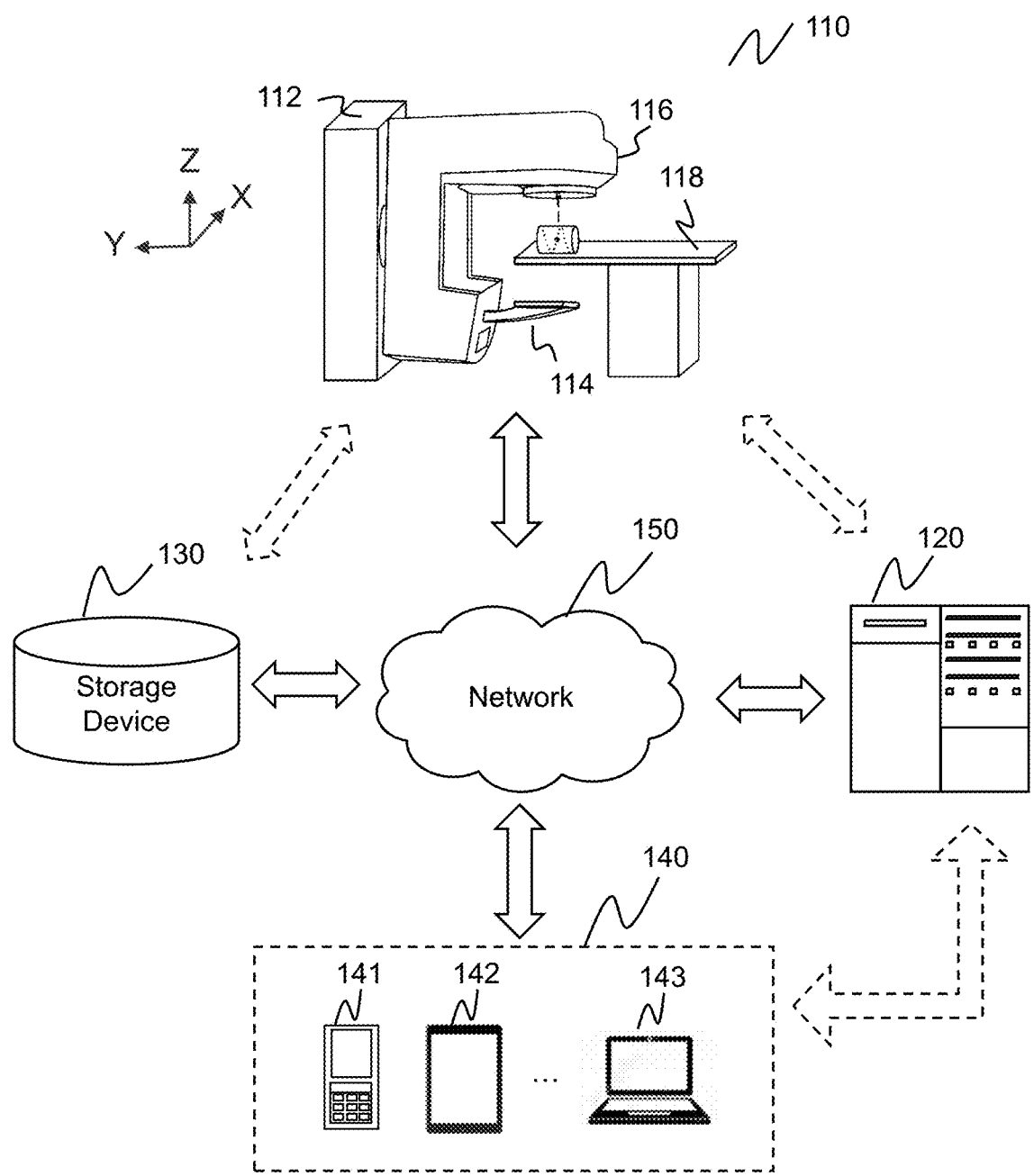
FIG. 1 is a schematic diagram illustrating an exemplary radiation system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. Also, the term "exemplary" is intended to refer to an example or illustration.

It will be understood that the terms "system," "engine," "unit," "module," and/or "block" used herein are one method to distinguish different components, elements, parts, sections or assembly of different levels in ascending order. However, the terms may be displaced by another expression if they achieve the same purpose.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that, although the terms "first," "second," "third," etc., may be used herein to describe various elements, these elements should not be limited by these terms. These terms are only used to distinguish one element from another. For example, a first element could be termed a second element, and, similarly, a second element could be termed a first element, without departing from the scope of exemplary embodiments of the present disclosure.

Spatial and functional relationships between elements are described using various terms, including "connected," "attached," and "mounted." Unless explicitly described as being "direct," when a relationship between first and second elements is described in the present disclosure, that relationship includes a direct relationship where no other intervening elements are present between the first and second elements, and also an indirect relationship where one or more intervening elements are present (either spatially or functionally) between the first and second elements. In contrast, when an element is referred to as being "directly" connected, attached, or positioned to another element, there are no intervening elements present. Other words used to describe the relationship between elements should be interpreted in a like fashion (e.g., "between," versus "directly between," "adjacent," versus "directly adjacent," etc.).

It should also be understood that terms such as "top," "bottom," "upper," "lower," "vertical," "lateral," "above," "below," "upward(s)," "downward(s)," "left-hand side," "right-hand side," "horizontal," and other such spatial reference terms are used in a relative sense to describe the positions or orientations of certain surfaces/parts/components of the radiation system with respect to other such features of the radiation system when the imaging device is in a normal operating position and may change if the position or orientation of the radiation system changes.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

For illustration purposes, the following description is provided to help better understanding a calibrating process. It is understood that this is not intended to limit the scope of the present disclosure. For persons having ordinary skills in the art, a certain amount of variations, changes and/or modifications may be deducted under the guidance of the present disclosure. Those variations, changes and/or modifications do not depart from the scope of the present disclosure.

An aspect of the present disclosure relates to a method for calibrating a radiation device. The radiation device may include a radiation source, a collimator, and a detector of an imaging device disposed opposite to the radiation source. The radiation source may be configured to emit a radiation beam. The collimator may be configured to adjust the radiation beam. According to some embodiments of the present disclosure, a plurality of images acquired by the imaging device at a plurality of source-to-image distances (SIDs) may be obtained. A plurality of offset distances between a plurality of first projection positions of a first axis of the collimator on the imaging device and a plurality of second projection positions of a second axis of the radiation beam on the imaging device (e.g., a detector of the imaging device) may be determined based on the plurality of images acquired at the plurality of SIDs. A determination may be made as to whether to calibrate the radiation device by comparing at least one offset distance of the plurality of offset distances with a first threshold. In some embodiments, a deviation between the first axis of the collimator and the second axis of the radiation beam may be determined based on the plurality of SIDs and the plurality of offset distances. A determination may be made as to whether to calibrate the radiation device by comparing the deviation with a second threshold. Therefore, the radiation device may be calibrated based on images acquired by the imaging device, without extensive calibration procedures, and accordingly the overall costs, processing and analysis time may be reduced. Furthermore, the radiation device may be calibrated without subjective human decisions, the calibration process may be simplified, automated and/or semi-automated, and accordingly the efficiency and/or the accuracy of the calibration process may be improved.

Figure 2:
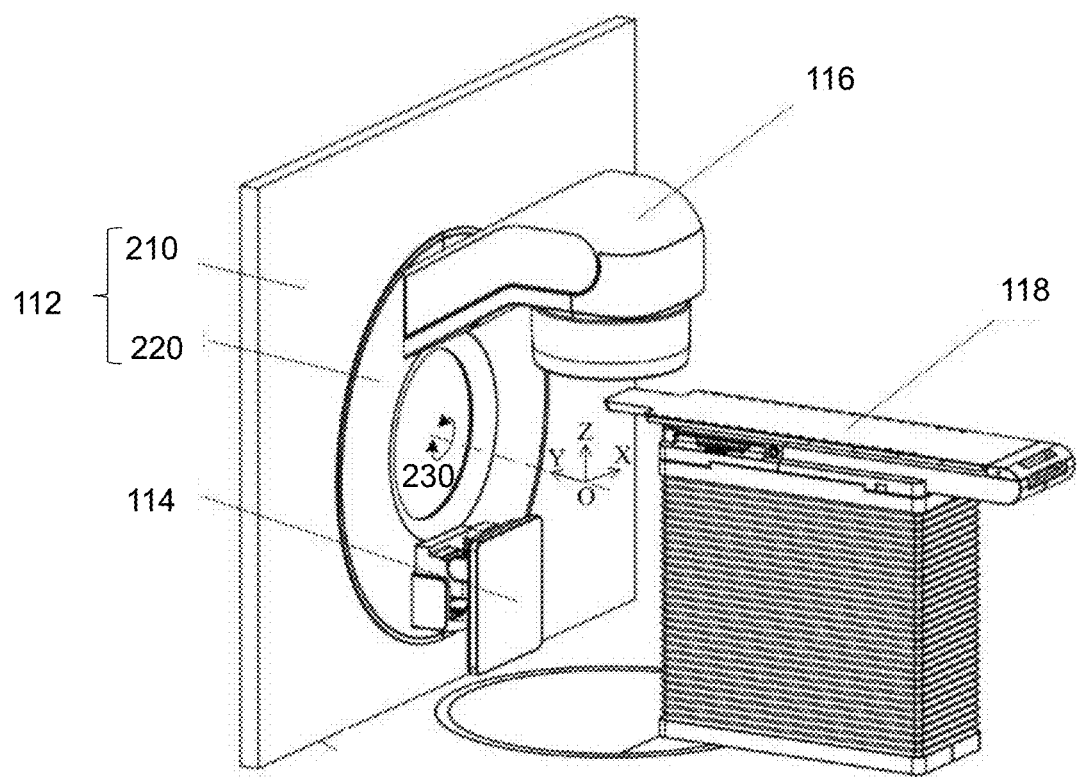
FIG. 2 is a schematic diagram illustrating an exemplary radiation device according to some embodiments of the present disclosure.
Figure 3:
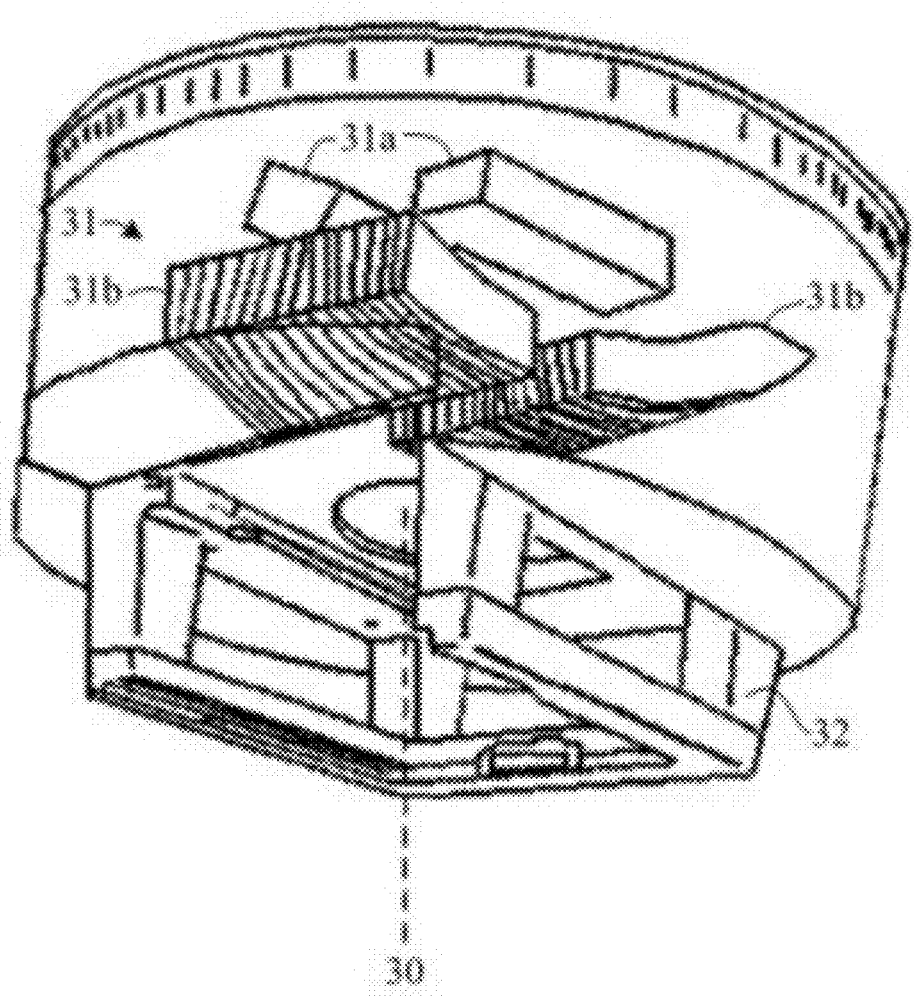
FIG. 3 is a schematic diagram illustrating an exemplary treatment head according to some embodiments of the present disclosure.

FIG. 1 is a schematic diagram illustrating an exemplary radiation system according to some embodiments of the present disclosure. FIG. 2 is a schematic diagram illustrating an exemplary radiation device according to some embodiments of the present disclosure. FIG. 3 is a schematic diagram illustrating an exemplary treatment head according to some embodiments of the present disclosure. As shown in FIG. 1, the radiation system 100 may include a radiation device 110, a processing device 120, a storage device 130, one or more terminal(s) 140, and a network 150. In some embodiments, the radiation device 110, the processing device 120, the storage device 130, and/or the terminal(s) 140 may be connected to and/or communicate with each other via a wireless connection (e.g., the network 150), a wired connection, or a combination thereof. The radiation system 100 may include various types of connection between its components. For example, the radiation device 110 may be connected to the processing device 120 through the network 150, or connected to the processing device 120 directly as illustrated by the bidirectional dotted arrow connecting the radiation device 110 and the processing device 120 in FIG. 1. As another example, the storage device 130 may be connected to the processing device 120 through the network 150, as illustrated in FIG. 1, or connected to the processing device 120 directly. As still another example, the storage device 130 may be connected to the radiation device 110 through the network 150, or connected to the radiation device 110 directly as illustrated by the bidirectional dotted arrow connecting the radiation device 110 and the storage device 130 in FIG. 1. As still another example, the terminal(s) 140 may be connected to the processing device 120 through the network 150, or connected to the processing device 120 directly as illustrated by the bidirectional dotted arrow connecting the terminal(s) 140 and the processing device 120 in FIG. 1. As still another example, the terminal(s) 140 may be connected to the radiation device 110 through the network 150, as illustrated in FIG. 1, or connected to the radiation device 110 directly.

The radiation device 110 may deliver a radiation beam to a subject (e.g., a patient) or a portion thereof. In some embodiments, the radiation device 110 may include a gantry 112, a detector 114, a treatment head 116, and a table 118. In the present disclosure, as shown in FIG. 1, a positive X axis direction may be from the right side to the left side of the gantry 112 viewed from the direction facing the front of the radiation device 110. A positive Y axis direction may be from the front part to the rear part of the gantry 112 along an axis of a scanning channel. A positive Z axis direction may be from the upper part to the lower part of the gantry 112.

The gantry 112 may be configured to support one or more components (e.g., the detector 114, the treatment head 116) of the radiation device 110. As shown in FIG. 2, the gantry 112 may include a fixed component 210 and a rotation component 220. The rotation component 220 may be installed on the fixed component 210. The rotation component 220 may rotate, for example, clockwise or counterclockwise around a gantry rotation axis 230 (i.e., the Y axis).

The treatment head 116 may be coupled to the gantry 112. In some embodiments, the treatment head 116 may be connected to the rotation component 220 of the gantry 112. In some embodiments, the treatment head 116 may rotate around a rotation axis (e.g., the gantry rotation axis 230) to be positioned at various gantry angles, such that the subject located in the table 118 may be imaged and/or treated from a plurality of directions. Merely by way of example, the treatment head 116 and the detector 114 may be movably or fixedly attached to the rotation component 220 of the gantry 112. When the gantry 112 rotates around the gantry rotation axis 230 in a circular path, the treatment head 116 and the detector 114 attached on the gantry 112 may rotate along with the gantry 112, and the subject located in the table 118 may be imaged and/or treated from a plurality of gantry angles. As used herein, a gantry angle may relate to a position of a radiation source in the treatment head 116 with reference to the radiation device 110. For example, a gantry angle may be an angle between a vertical direction (i.e., the Z axis direction) and a direction of a beam axis of a radiation beam emitted from the radiation source of the radiation device 110.

In some embodiments, as shown in FIG. 3, the treatment head 116 may include the radiation source (not shown), a collimator 31, and an auxiliary component 32. In some embodiments, the radiation source may include an imaging radiation source and a treatment radiation source. The imaging radiation source may be configured to emit an imaging beam to a subject. The imaging beam may include a particle beam, a photon beam, or the like, or any combination thereof. The particle beam may include a stream of neutrons, protons, electrons, heavy ions, or the like, or any combination thereof. The photon beam may include an X-ray beam, a γ-ray beam, an α-ray beam, a β-ray beam, an ultraviolet beam, a laser beam, or the like, or any combination thereof. The energy level of the imaging beam may be suitable for imaging. In some embodiments, an X-ray beam delivered by the imaging radiation source may have an energy of a kilovoltage (kV) level. Merely by way of example, the energy of the X-ray beam may be 90 kV.

The treatment radiation source may be configured to deliver a treatment beam to a subject. The treatment beam may include a particle beam, a photon beam, an ultrasound beam (e.g., a high intensity focused ultrasound beam), or the like, or any combination thereof. The particle beam may include a stream of neutrons, protons, electrons, heavy ions, or the like, or any combination thereof. The photon beam may include an X-ray beam, a γ-ray beam, an α-ray beam, a β-ray beam, an ultraviolet beam, a laser beam, or the like, or any combination thereof. The energy level of the treatment beam may be suitable for radiotherapy. For example, an X-ray beam delivered by the treatment radiation source may have an energy of the megavoltage (MV) level. Merely by way of example, the energy of the X-ray beam emitted by the treatment radiation source may be 6 MV.

In some embodiments, the radiation source may be a homologous dual-beam accelerator. In some embodiments, one radiation source may be used as both the imaging radiation source and the treatment radiation source to image and/or treat a subject. In the present disclosure, both an imaging beam and a treatment beam may also be referred to as a radiation beam.

The collimator 31 may be configured to adjust a shape of a radiation beam (e.g., the imaging beam, the treatment beam) emitted from the radiation source. The radiation beam may pass through one or more collimators 31 of certain configuration(s), and enter into a subject. In some embodiments, as shown in FIG. 3, the collimator 31 may include a first beam adjustment component 31a and a second beam adjustment component 31b. The first beam adjustment component 31a and the second beam adjustment component 31b may include a jaw, a multi-leaf collimator (MLC), or the like. The MLC may include a plurality of leaves that form an aperture. The aperture may modify the shape of a radiation beam passing through the aperture. For example, a portion of the radiation beam may pass through the aperture, and other portions of the radiation beam may be blocked or partially blocked by the leaves of the MLC.

In some embodiments, the collimator 31 may be rotated around a rotation axis 30 of the collimator 31 (also referred to as a first axis of the collimator 31). In some embodiments, the first beam adjustment component 31a and the second beam adjustment component 31b of the collimator 31 may move during the rotation of the collimator 31 according to a treatment plan to generate a desired shape for the radiation beam that passes through the collimator 31.

The auxiliary component 32 may be configured to accommodate one or more components (e.g., a marker board, a wedge block) of the treatment head 116. The marker board may include a reticle, a translucent metal board (e.g., a translucent metal board with a center circle), or the like, or any combination thereof. In some embodiments, the auxiliary component 32 may be rotated around the rotation axis 30 as the collimator 31 rotates around the rotation axis 30. That is, during the rotation of the collimator 31 around the rotation axis 30, the positional relationship between the collimator 31 and the auxiliary component 32 is fixed.

The detector 114 may be placed on the rotation component 220 of the gantry 112 opposite to the radiation source. The detector 114 may be configured to detect and/or receive radiation associated with the beams (e.g., X-ray beams) emitted from the radiation source. The detector 114 may detect and/or receive radiation associated with the beams emitted from the radiation source during and/or before a treatment operation or an imaging operation. For example, during a treatment operation, the detector 114 may detect the radiation associated with the beams emitted from the radiation source and monitor the condition (e.g., a radiation dose) of the treatment operation. As another example, before the treatment operation, the radiation source may deliver a pre-treatment beam, and the detector 114 may detect radiation associated with at least portion of the pre-treatment beam for calibration (e.g., a calibration of the radiation beam). In some embodiments, the shape of the detector 114 may be flat, arc-shaped, circular, or the like, or any combination thereof. For example, the detector 114 may be a flat panel detector configured to detect radiation emitted by the radiation source after attenuation by a subject.

In some embodiments, a combination of the imaging radiation source and the detector 114 (also referred to as an imaging device) may be configured to provide image data for generating an image associated with a subject. In some embodiments, the image (e.g., a CT image, a cone beam computed tomography (CBCT) image, an MRI image, a PET image, a PET-CT image) associated with the subject may be generated according to image data acquired by the detector 114.

In some embodiments, the detector 114 may be an electronic portal imaging device (EPID). The EPID may be used to measure an X-ray intensity transmitted through a subject from the radiation source during a treatment operation. The radiation signal may be converted electronically into a two-dimensional (2D) digital radiographic image to verify the correct beam placement in relation to the subject's anatomy. In some embodiments, the detector 114 may transmit the image(s) to the processing device 120, the storage device 130, and/or the terminal(s) 140 via the network 150. For example, the image(s) may be sent to the processing device 120 for further processing or may be stored in the storage device 130.

The table 118 may be configured to support a subject (e.g., a patient) and/or transport the subject to the gantry 112, where the subject may be to be imaged and/or treated. The table 118 may be adjustable and/or movable to suit for different application scenarios.

In some embodiments, the subject to be treated or imaged may include a body, substance, or the like, or any combination thereof. In some embodiments, the subject may include a specific portion of a body, such as a head, a thorax, an abdomen, or the like, or any combination thereof. In some embodiments, the subject may include a specific organ, such as a breast, an esophagus, a trachea, a bronchus, a stomach, a gallbladder, a small intestine, a colon, a bladder, a ureter, a uterus, a fallopian tube, etc. In the present disclosure, "object" and "subject" are used interchangeably.

The processing device 120 may process data and/or information obtained from the radiation device 110, the storage device 130, and/or the terminal(s) 140. For example, the processing device 120 may obtain at least one image acquired at at least one source-to-image distance (SID) acquired by an imaging device. As another example, the processing device 120 may determine, based on at least one image acquired at at least one SID, at least one offset distance between a first projection position of a first axis of a collimator (e.g., the collimator 31) on an imaging device and a second projection position of a second axis of a radiation beam on the imaging device. As a further example, the processing device 120 may determine whether to calibrate a radiation device (e.g., the radiation device 110) by comparing at least one offset distance with a threshold. As a further example, the processing device 120 may adjust at least one component (e.g., an acceleration tube, a target) in a radiation device (e.g., the radiation device 110) in response to a determination that at least one offset distance exceeds a threshold. As a still further example, the processing device 120 may determine, based on a plurality of images acquired at a plurality of SIDs, a plurality of offset distances between a plurality of first projection positions of a first axis of a collimator (e.g., the collimator 31) on an imaging device and a plurality of second projection positions of a second axis of a radiation beam on the imaging device. As a still further example, the processing device 120 may determine, based on a plurality of SIDs and a plurality of offset distances, a deviation between a first axis of a collimator (e.g., the collimator 31) and a second axis of a radiation beam. As a still further example, the processing device 120 may determine whether to calibrate a radiation device (e.g., the radiation device 110) by comparing a deviation between a first axis of a collimator (e.g., the collimator 31) and a second axis of a radiation beam with a threshold. In some embodiments, the processing device 120 may be a single server or a server group. The server group may be centralized or distributed. In some embodiments, the processing device 120 may be local or remote. For example, the processing device 120 may access information and/or data from the radiation device 110, the storage device 130, and/or the terminal(s) 140, via the network 150. As another example, the processing device 120 may be directly connected to the radiation device 110, the terminal(s) 140, and/or the storage device 130 to access information and/or data. In some embodiments, the processing device 120 may be implemented on a cloud platform. For example, the cloud platform may include a private cloud, a public cloud, a hybrid cloud, a community cloud, a distributed cloud, an inter-cloud, a multi-cloud, or the like, or a combination thereof. In some embodiments, the processing device 120 may be part of the terminal 140. In some embodiments, the processing device 120 may be part of the radiation device 110.

The storage device 130 may store data, instructions, and/or any other information. In some embodiments, the storage device 130 may store data obtained from the radiation device 110, the processing device 120, and/or the terminal(s) 140. For example, the storage device 130 may store at least one image acquired at at least one SID acquired by an imaging device. As another example, the storage device 130 may store a deviation between a first axis of a collimator (e.g., the collimator 31) and a second axis of a radiation beam determined by the processing device 120. As still another example, the storage device 130 may store at least one offset distance between a first projection position of a first axis of a collimator (e.g., the collimator 31) on an imaging device and a second projection position of a second axis of a radiation beam on the imaging device determined by the processing device 120. In some embodiments, the storage device 130 may store data and/or instructions that the processing device 120 and/or the terminal 140 may execute or use to perform exemplary methods described in the present disclosure. In some embodiments, the storage device 130 may include a mass storage, a removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 130 may be implemented on a cloud platform as described elsewhere in the disclosure.

In some embodiments, the storage device 130 may be connected to the network 150 to communicate with one or more other components in the radiation system 100 (e.g., the processing device 120, the terminal(s) 140). One or more components in the radiation system 100 may access the data or instructions stored in the storage device 130 via the network 150.

The terminal(s) 140 may be connected to and/or communicate with the radiation device 110, the processing device 120, and/or the storage device 130. In some embodiments, the terminal 140 may include a mobile device 141, a tablet computer 142, a laptop computer 143, or the like, or any combination thereof. For example, the mobile device 141 may include a mobile phone, a personal digital assistant (PDA), a gaming device, a navigation device, a point of sale (POS) device, a laptop, a tablet computer, a desktop, or the like, or any combination thereof. In some embodiments, the terminal 140 may include an input device, an output device, etc. The input device may include alphanumeric and other keys that may be input via a keyboard, a touchscreen (for example, with haptics or tactile feedback), a speech input, an eye tracking input, a brain monitoring system, or any other comparable input mechanism. Other types of the input device may include a cursor control device, such as a mouse, a trackball, or cursor direction keys, etc. The output device may include a display, a printer, or the like, or any combination thereof.

The network 150 may include any suitable network that can facilitate the exchange of information and/or data for the radiation system 100. In some embodiments, one or more components of the radiation system 100 (e.g., the radiation device 110, the processing device 120, the storage device 130, the terminal(s) 140, etc.) may communicate information and/or data with one or more other components of the radiation system 100 via the network 150. For example, the processing device 120 and/or the terminal 140 may obtain at least one image acquired at at least one SID from the radiation device 110 via the network 150. As another example, the processing device 120 and/or the terminal 140 may obtain information stored in the storage device 130 via the network 150. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network (VPN), a satellite network, a telephone network, routers, hubs, witches, server computers, and/or any combination thereof. For example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the radiation system 100 may be connected to the network 150 to exchange data and/or information.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. However, those variations and modifications do not depart the scope of the present disclosure. In some embodiments, the storage device 130 may be data storage including cloud computing platforms, such as a public cloud, a private cloud, community, and hybrid clouds, or the like. In some embodiments, the radiation system 100 may further include a control device (not shown in FIG. 1). The control device may be configured to receive an instruction provided by an user for controlling an operation status of at least one component (e.g., the treatment head 116, the gantry 112, the table 118) of the radiation device 110. For example, the control device may control a rotation angle, a rotation time of the rotation component 220 of the gantry 112. As another example, the control device may control a shape, an intensity of a radiation beam emitted from the treatment head 116. As still another example, the control device may control a scanning time of a subject by the imaging device. As still another example, the control device may control a moving status of the table 118.

Figure 4:
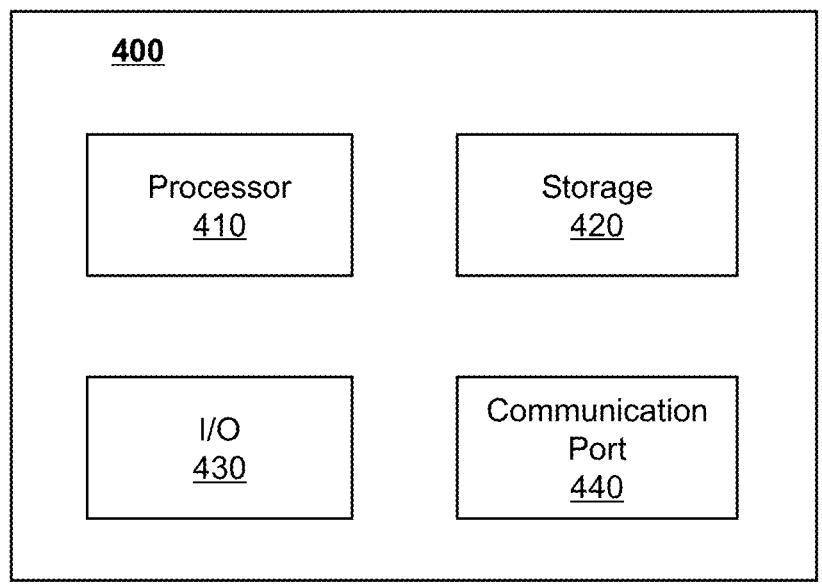
FIG. 4 is a schematic diagram illustrating exemplary hardware and/or software components of an exemplary computing device on which the processing device may be implemented according to some embodiments of the present disclosure.

FIG. 4 is a schematic diagram illustrating exemplary hardware and/or software components of an exemplary computing device 400 on which the processing device 120 may be implemented according to some embodiments of the present disclosure. As illustrated in FIG. 4, the computing device 400 may include a processor 410, a storage 420, an input/output (I/O) 430, and a communication port 440.

The processor 410 may execute computer instructions (e.g., program code) and perform functions of the processing device 120 in accordance with techniques described herein. The computer instructions may include, for example, routines, programs, objects, components, data structures, procedures, modules, and functions, which perform particular functions described herein. For example, the processor 410 may process imaging data obtained from the radiation device 110, the terminal(s) 140, the storage device 130, and/or any other component of the radiation system 100. In some embodiments, the processor 410 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combination thereof.

Merely for illustration, only one processor is described in the computing device 400. However, it should be noted that the computing device 400 in the present disclosure may also include multiple processors. Thus operations and/or method steps that are performed by one processor as described in the present disclosure may also be jointly or separately performed by the multiple processors. For example, if in the present disclosure the processor of the computing device 400 executes both process A and process B, it should be understood that process A and process B may also be performed by two or more different processors jointly or separately in the computing device 400 (e.g., a first processor executes process A and a second processor executes process B, or the first and second processors jointly execute processes A and B).

The storage 420 may store data/information obtained from the radiation device 110, the terminal(s) 140, the storage device 130, and/or any other component of the radiation system 100. The storage 420 may be similar to the storage device 130 described in connection with FIG. 1, and the detailed descriptions are not repeated here.

The I/O 430 may input and/or output signals, data, information, etc. In some embodiments, the I/O 430 may enable a user interaction with the processing device 120. In some embodiments, the I/O 430 may include an input device and an output device. Examples of the input device may include a keyboard, a mouse, a touchscreen, a microphone, a sound recording device, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touchscreen, or the like, or a combination thereof.

The communication port 440 may be connected to a network (e.g., the network 150) to facilitate data communications. The communication port 440 may establish connections between the processing device 120 and the radiation device 110, the terminal(s) 140, and/or the storage device 130. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee link, a mobile network link (e.g., 3G, 4G, 5G), or the like, or any combination thereof. In some embodiments, the communication port 440 may be and/or include a standardized communication port, such as RS232, RS485. In some embodiments, the communication port 440 may be a specially designed communication port. For example, the communication port 440 may be designed in accordance with the digital imaging and communications in medicine (DICOM) protocol.

Figure 5:
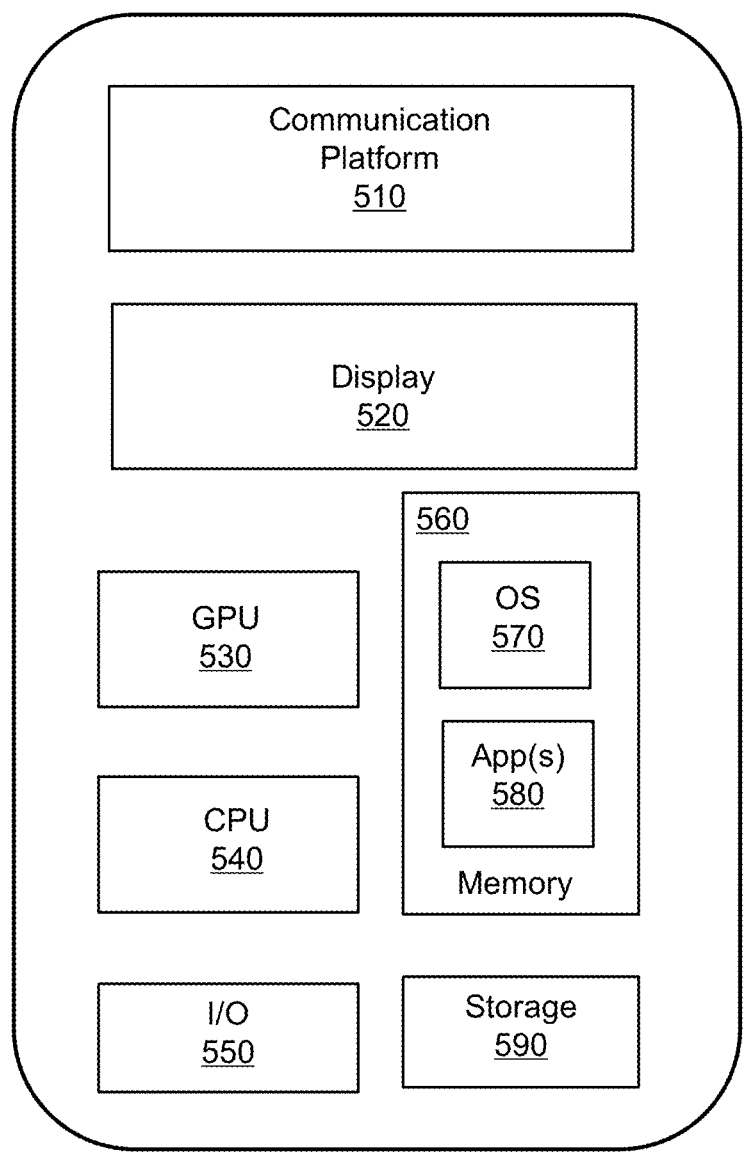
FIG. 5 is a schematic diagram illustrating exemplary hardware and/or software components of an exemplary mobile device on which the terminal(s) may be implemented according to some embodiments of the present disclosure.

FIG. 5 is a schematic diagram illustrating exemplary hardware and/or software components of an exemplary mobile device 500 on which the terminal(s) 140 may be implemented according to some embodiments of the present disclosure.

As illustrated in FIG. 5, the mobile device 500 may include a communication platform 510, a display 520, a graphics processing unit (GPU) 530, a central processing unit (CPU) 540, an I/O 550, a memory 560, and a storage 590. In some embodiments, any other suitable component, including but not limited to a system bus or a controller (not shown), may also be included in the mobile device 500.

In some embodiments, the communication platform 510 may be configured to establish a connection between the mobile device 500 and other components of the radiation system 100, and enable data and/or signal to be transmitted between the mobile device 500 and other components of the radiation system 100. For example, the communication platform 510 may establish a wireless connection between the mobile device 500 and the radiation device 110, and/or the processing device 120. The wireless connection may include, for example, a Bluetooth™ link, a Wi-Fi™ link, a WiMax™ link, a WLAN link, a ZigBee link, a mobile network link (e.g., 3G, 4G, 5G), or the like, or any combination thereof. The communication platform 510 may also enable the data and/or signal between the mobile device 500 and other components of the radiation system 100. For example, the communication platform 510 may transmit data and/or signals inputted by a user to other components of the radiation system 100. The inputted data and/or signals may include a user instruction. As another example, the communication platform 510 may receive data and/or signals transmitted from the processing device 120. The received data and/or signals may include imaging data acquired by the detector 114 of the radiation device 110.

In some embodiments, a mobile operating system (OS) 570 (e.g., iOS™, Android™, Windows Phone™, etc.) and one or more applications (App(s)) 580 may be loaded into the memory 560 from the storage 590 in order to be executed by the CPU 540. The applications 580 may include a browser or any other suitable mobile apps for receiving and rendering information respect to a calibration process or other information from the processing device 120. User interactions with the information stream may be achieved via the I/O 550 and provided to the processing device 120 and/or other components of the radiation system 100 via the network 150.

To implement various modules, units, and their functionalities described in the present disclosure, computer hardware platforms may be used as the hardware platform(s) for one or more of the elements described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result the drawings should be self-explanatory.

Figure 6:
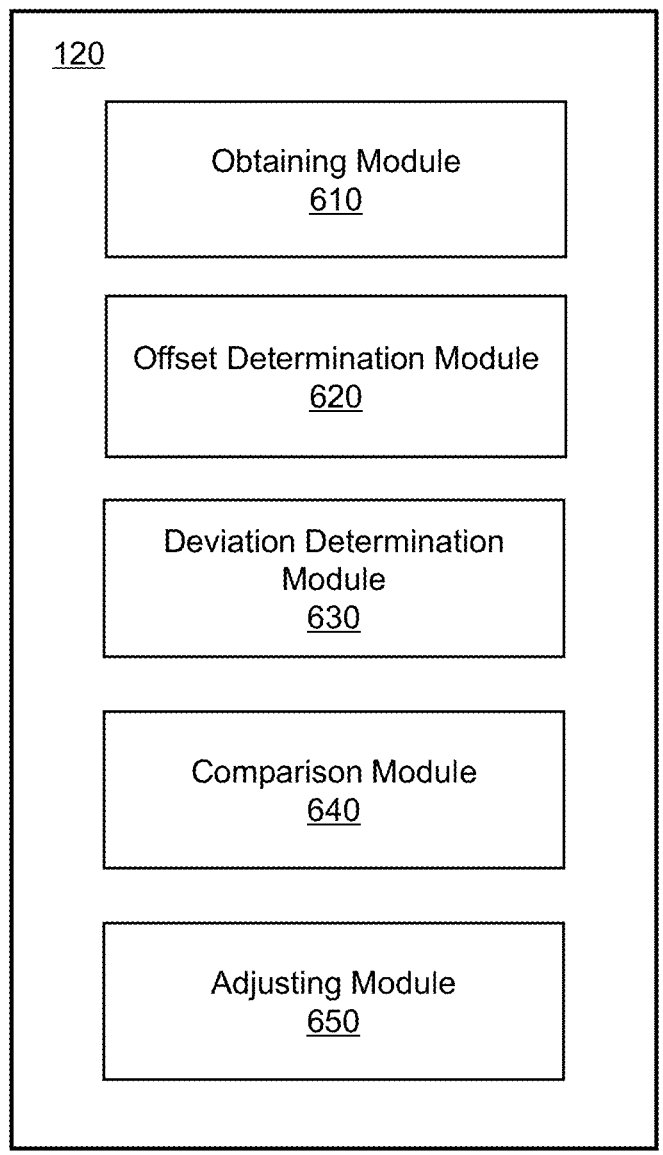
FIG. 6 is a schematic diagram illustrating an exemplary processing device according to some embodiments of the present disclosure.

FIG. 6 is a schematic diagram illustrating an exemplary processing device according to some embodiments of the present disclosure. In some embodiments, the processing device 120 may include an obtaining module 610, an offset determination module 620, a deviation determination module 630, a comparison module 640, and an adjusting module 650. The modules may be hardware circuits of at least part of the processing device 120. The modules may also be implemented as an application or set of instructions read and executed by the processing device 120. Further, the modules may be any combination of the hardware circuits and the application/instructions. For example, the modules may be part of the processing device 120 when the processing device 120 is executing the application or set of instructions.

The obtaining module 610 may be configured to obtain data and/or information associated with the radiation system 100. The data and/or information associated with the radiation system 100 may include an image, an offset distance, a deviation, a threshold, or the like, or any combination thereof. In some embodiments, the obtaining module 610 may obtain a plurality of images acquired at each SID of at least one SID by an imaging device. For example, the obtaining module 610 may obtain at least one first image acquired at an SID by an imaging device. As another example, the obtaining module 610 may obtain at least one second image acquired at an SID by an imaging device. In some embodiments, the obtaining module 610 may obtain the data and/or the information associated with the radiation system 100 from one or more components (e.g., the radiation device 110, the storage device 130, the terminal 140) of the radiation system 100 via the network 150.

The offset determination module 620 may be configured to determine an offset distance between a first projection position of a first axis of a collimator on an imaging device and a second projection position of a second axis of a radiation beam on the imaging device. In some embodiments, the offset determination module 620 may determine an offset distance associated with an SID based on a plurality of images acquired at an SID. For example, the offset determination module 620 may determine a first projection position of a first axis of a collimator on an imaging device based on at least one first image acquired at an SID. The offset determination module 620 may determine a second projection position of a second axis of a radiation beam on the imaging device based on at least one second image acquired at the SID. The offset determination module 620 may determine an offset distance associated with the SID based on the first projection position of the first axis of the collimator on the imaging device and the second projection position of the second axis of the radiation beam on the imaging device.

The deviation determination module 630 may be configured to determine a deviation between a first axis of a collimator and a second axis of a radiation beam. In some embodiments, the deviation determination module 630 may determine a deviation between a first axis of a collimator and a second axis of a radiation beam based on a plurality of SIDs and a plurality of offset distances. More descriptions of the determination of the deviation may be found elsewhere in the present disclosure (e.g., FIGS. 9, 10, and descriptions thereof).

The comparison module 640 may be configured to compare data and/or information associated with the radiation system 100. For example, the comparison module 640 may determine whether to calibrate a radiation device (e.g., the radiation device 110) by comparing at least one offset distance with a threshold. As another example, the comparison module 640 may determine whether to calibrate a radiation device (e.g., the radiation device 110) by comparing a deviation between a first axis of a collimator and a second axis of a radiation beam with a threshold.

The adjusting module 650 may be configured to adjust at least one component in a radiation device (e.g., the radiation device 110). For example, the adjusting module 650 may adjust a position of at least one component (e.g., an acceleration tube, a target) in a radiation device.

It should be noted that the above description of the processing device 120 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more modules may be combined into a single module. For example, the offset determination module 620 and the deviation determination module 630 may be combined into a single module, which may both determine an offset distance and a deviation. In some embodiments, one or more modules may be added or omitted in the processing device 120. For example, the processing device 120 may further include a storage module (not shown in FIG. 6) configured to store data and/or information (e.g., a plurality of images, a plurality of offset distances, a deviation) associated with the radiation system 100.

Figure 7:
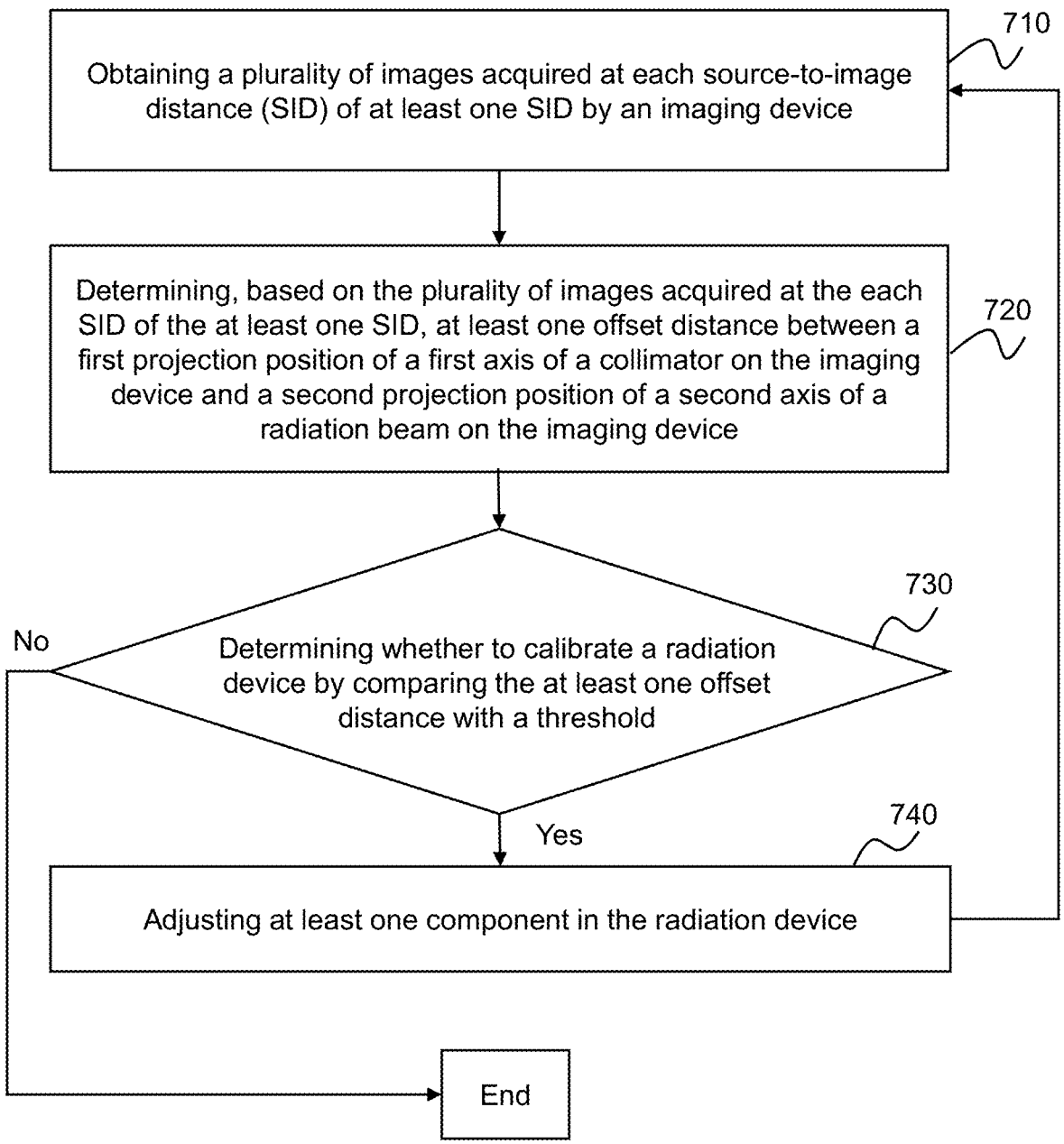
FIG. 7 is a flowchart illustrating an exemplary process for calibrating a radiation device according to some embodiments of the present disclosure.

FIG. 7 is a flowchart illustrating an exemplary process for calibrating a radiation device according to some embodiments of the present disclosure. In some embodiments, the process 700 may be implemented in the radiation system 100 illustrated in FIG. 1. For example, the process 700 may be stored in the storage device 130 and/or the storage (e.g., the storage 420, the storage 590) as a form of instructions, and invoked and/or executed by the processing device 120 (e.g., the processor 410 of the computing device 400 as illustrated in FIG. 4, the CPU 540 of the mobile device 500 as illustrated in FIG. 5). The operations of the illustrated process presented below are intended to be illustrative. In some embodiments, the process 700 may be accomplished with one or more additional operations not described, and/or without one or more of the operations discussed. Additionally, the order in which the operations of the process 700 as illustrated in FIG. 7 and described below is not intended to be limiting.

In 710, the processing device 120 (e.g., the obtaining module 610) may obtain a plurality of images acquired at each source-to-image distance (SID) of at least one SID by an imaging device.

As used herein, the SID may refer to a distance measured between a focal spot target on an X-ray tube to an image receptor (e.g., an X-ray detector) as measured along a beam axis of a radiation beam generated by and emitted from the X-ray tube. In some embodiments, the SID may be manually set by a user of the radiation system 100, or determined by one or more components of the radiation system 100. In some embodiments, the processing device 120 may determine the SID according to a laser ranging technique.

The plurality of images may include at least one first image and at least one second image. In some embodiments, at each SID of the at least one SID, the imaging device may generate one or more first images and one or more second images. The first image may be used for determining a first projection position of a first axis (e.g., the rotation axis 30) of a collimator (e.g., the collimator 31) on the imaging device (e.g., the detector 114 of the imaging device). In some embodiments, the processing device 120 may obtain the first image by rotating the collimator around the first axis of the collimator. In some embodiments, the first image may be a projection image of a marker board in the collimator. For example, the marker board may be inserted into an auxiliary component (e.g., the auxiliary component 32) of the collimator (e.g., the collimator 31). The imaging device may generate the projection image of the marker board by rotating the collimator around the first axis of the collimator to at least one gantry angle. In some embodiments, the first image may be a projection image of a beam adjustment component (e.g., the first beam adjustment component 31*a*, the second beam adjustment component 31*b*) of the collimator (e.g., the collimator 31). The first beam adjustment component 31*a* and the second beam adjustment component 31*b* may include a jaw, a multi-leaf collimator (MLC), or the like. For example, the imaging device may generate the projection image of the beam adjustment component by rotating the collimator around the first axis of the collimator to at least one gantry angle.

The second image may be used for determining a second projection position of a second axis (also referred to as a beam axis) of a radiation beam on the imaging device (e.g., the detector 114 of the imaging device). In some embodiments, the processing device 120 may obtain the second image using a phantom. The phantom may include a ball bearing (BB) phantom. In some embodiments, the second image may be a projection image of the phantom collected from at least one gantry angle. For example, a treatment head (the treatment head 116) may be fixedly attached to a gantry (e.g., the gantry 112) while a detector (e.g., the detector 114) may be fixedly or flexibly attached to the gantry (e.g., the gantry 112) opposite to the treatment head. As used herein, a fixed attachment of component A (e.g., the treatment head 116) to component B (e.g., the gantry 112) may indicate that the component A does not move relatively to the component B when the component A and the component B are properly assembled and used as intended. As used herein, a flexible attachment of component A (e.g., the treatment head 116) to component B (e.g., the gantry 112) may indicate that the component A can move relatively to the component B when the component A and the component B are properly assembled and used as intended. When the gantry 112 rotates around a rotation axis (e.g., the gantry rotation axis 230), the treatment head and the detector may rotate along with the gantry 112, and the phantom may be imaged from a plurality of gantry angles. In some embodiments, the phantom may be imaged every time the gantry angle changes 1° for a total change of 360°.

In some embodiments, the processing device 120 may obtain the plurality of images (e.g., the first image, the second image) from the imaging device periodically (e.g., per second, per 2 seconds, per 5 seconds, per 10 seconds) or in real time. In some embodiments, the imaging device may transmit a plurality of images to a storage device (e.g., the storage device 130) periodically (e.g., per second, per 2 seconds, per 5 seconds, per 10 seconds) or in real time via the network 150. Further, the processing device 120 may access the storage device and retrieve the at least one image.

In 720, the processing device 120 (e.g., the offset determination module 620) may determine, based on the plurality of images acquired at each SID of the at least one SID, at least one offset distance between a first projection position of a first axis of a collimator on the imaging device and a second projection position of a second axis of a radiation beam on the imaging device.

In some embodiments, at the each SID of the at least one SID, the processing device 120 may determine the first projection position of the first axis of the collimator on the imaging device based on the at least one first image acquired at the SID. The processing device 120 may determine the second projection position of the second axis of the radiation beam on the imaging device based on the at least one second image acquired at the SID. The processing device 120 may determine an offset distance associated with the SID based on the first projection position of the first axis of the collimator on the imaging device and the second projection position of the second axis of the radiation beam on the imaging device. More descriptions of the determination of an offset distance associated with an SID may be found elsewhere in the present disclosure (e.g., FIG. 8, and descriptions thereof).

In 730, the processing device 120 (e.g., the comparison module 640) may determine whether to calibrate a radiation device (e.g., the radiation device 110) by comparing the at least one offset distance with a threshold.

In some embodiments, the threshold may be a default parameter stored in a storage device (e.g., the storage device 130). Additionally or alternatively, the threshold may be set manually by a user of the radiation system 100, or determined by one or more components (e.g., the processing device 120) of the radiation system 100 according to different situations. In some embodiments, different offset distances associated with different SIDs may correspond to a same threshold. In some embodiments, different offset distances associated with different SIDs may correspond to different thresholds.

In some embodiments, the processing device 120 may determine the threshold based on historical data associated with a plurality of historical treatment operations and/or a plurality of historical imaging operations. For example, for each SID of the at least one SID, the processing device 120 may determine a plurality of offset distances in the plurality of historical treatment operations and/or the plurality of historical imaging operations that satisfy a treatment need and/or an imaging need. The processing device 120 may determine an average offset distance of the plurality of offset distances as the threshold corresponding to the SID.

In some embodiments, the processing device 120 may determine whether each offset distance of the at least one offset distance exceeds a threshold corresponding to the SID associated with the each offset distance. In response to a determination that an offset distance of the at least one offset distance exceeds the threshold corresponding to the SID associated with the offset distance, the processing device 120 may determine that the radiation device needs to be calibrated. In some embodiments, the processing device 120 may determine whether an average offset distance of the at least one offset distance is less than a threshold. In response to a determination that the average offset distance exceeds the threshold, the processing device 120 may determine that the radiation device needs to be calibrated, process 700 may proceed to operation 740.

In 740, the processing device 120 (e.g., the adjusting module 650) may adjust at least one component in the radiation device (e.g., the radiation device 110).

For example, the processing device 120 may adjust a position of the at least one component (e.g., an acceleration tube, a target) in the radiation device. In some embodiments, the at least one component (e.g., an acceleration tube, a target) in the radiation device may be adjusted automatically by other one or more components (e.g., the processing device 120, the terminal 140) of the radiation system 100, or adjusted manually by a user of the radiation system 100. After the position of the at least one component in the radiation device is adjusted, process 700 may return to operation 710. Operation 710 to operation 740 may be repeated until the processing device 120 determines that the at least one offset distance is less than the threshold.

In response to a determination that the at least one offset distance is less than the threshold, the processing device 120 may determine that the radiation device does not need to be calibrated, process 700 may end. The radiation device 110 may image and/or treat a subject. For example, the processing device 120 may send instructions that cause the treatment head 116 to emit the radiation beam to image and/or treat the subject. It should be noted that, in response to a determination that the at least one offset distance is equal to the threshold, the processing device 120 may either determine that the radiation device needs to be calibrated or determine that the radiation device does not need to be calibrated.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, two or more operations may be combined into a single operation. For example, operation 710 and operation 720 may be combined into a single operation.

FIG. 8 is a flowchart illustrating an exemplary process for determining an offset distance associated with an SID according to some embodiments of the present disclosure. In some embodiments, the process 800 may be implemented in the radiation system 100 illustrated in FIG. 1. For example, the process 800 may be stored in the storage device 130 and/or the storage (e.g., the storage 420, the storage 590) as a form of instructions, and invoked and/or executed by the processing device 120 (e.g., the processor 410 of the computing device 400 as illustrated in FIG. 4, the CPU 540 of the mobile device 500 as illustrated in FIG. 5). The operations of the illustrated process presented below are intended to be illustrative. In some embodiments, the process 800 may be accomplished with one or more additional operations not described, and/or without one or more of the operations discussed. Additionally, the order in which the operations of the process 800 as illustrated in FIG. 8 and described below is not intended to be limiting.

In 810, the processing device 120 (e.g., the offset determination module 620) may determine, based on at least one first image acquired at an SID, a first projection position of a first axis of a collimator on an imaging device.

In some embodiments, a first image may include a projection image of a marker board, a jaw, a multi-leaf collimator, or the like. In some embodiments, the processing device 120 may obtain the first image by rotating the collimator around the first axis of the collimator. For example, the processing device 120 may obtain one or more projection images of the marker board, the jaw, or the multi-leaf collimator by rotating the collimator around the first axis of the collimator from at least one gantry angle as described in connection with operation 710.

In some embodiments, the processing device 120 may determine a rotation center of the marker board, the jaw, the multi-leaf collimator, or the like, in the at least one first image as the first projection position of the first axis of the collimator on the imaging device.

In some embodiments, the processing device 120 may determine the first projection position of the first axis of the collimator on the imaging device based on a plurality of first images acquired at the SID. For example, the processing device 120 may determine an initial first projection position of the first axis of the collimator on the imaging device based on each first image of the plurality of first images. The processing device 120 may determine the first projection position of the first axis of the collimator on the imaging device based on a plurality of initial first projection positions of the first axis of the collimator on the imaging device by performing a fitting operation. As another example, the processing device 120 may determine an average image of the plurality of first images. In some embodiments, the processing device 120 may determine the average image of the plurality of first images based on a pixel value of each pixel of a plurality of pixels in each of the plurality of first images. For example, the processing device 120 may determine an average pixel value of a plurality of pixels in the plurality of first images. The processing device 120 may determine the average image based on a plurality of average pixel values. The processing device 120 may determine the first projection position of the first axis of the collimator on the imaging device based on the average image.

In 820, the processing device 120 (e.g., the offset determination module 620) may determine, based on at least one second image acquired at the SID, a second projection position of a second axis of a radiation beam on the imaging device.

Figure 11:
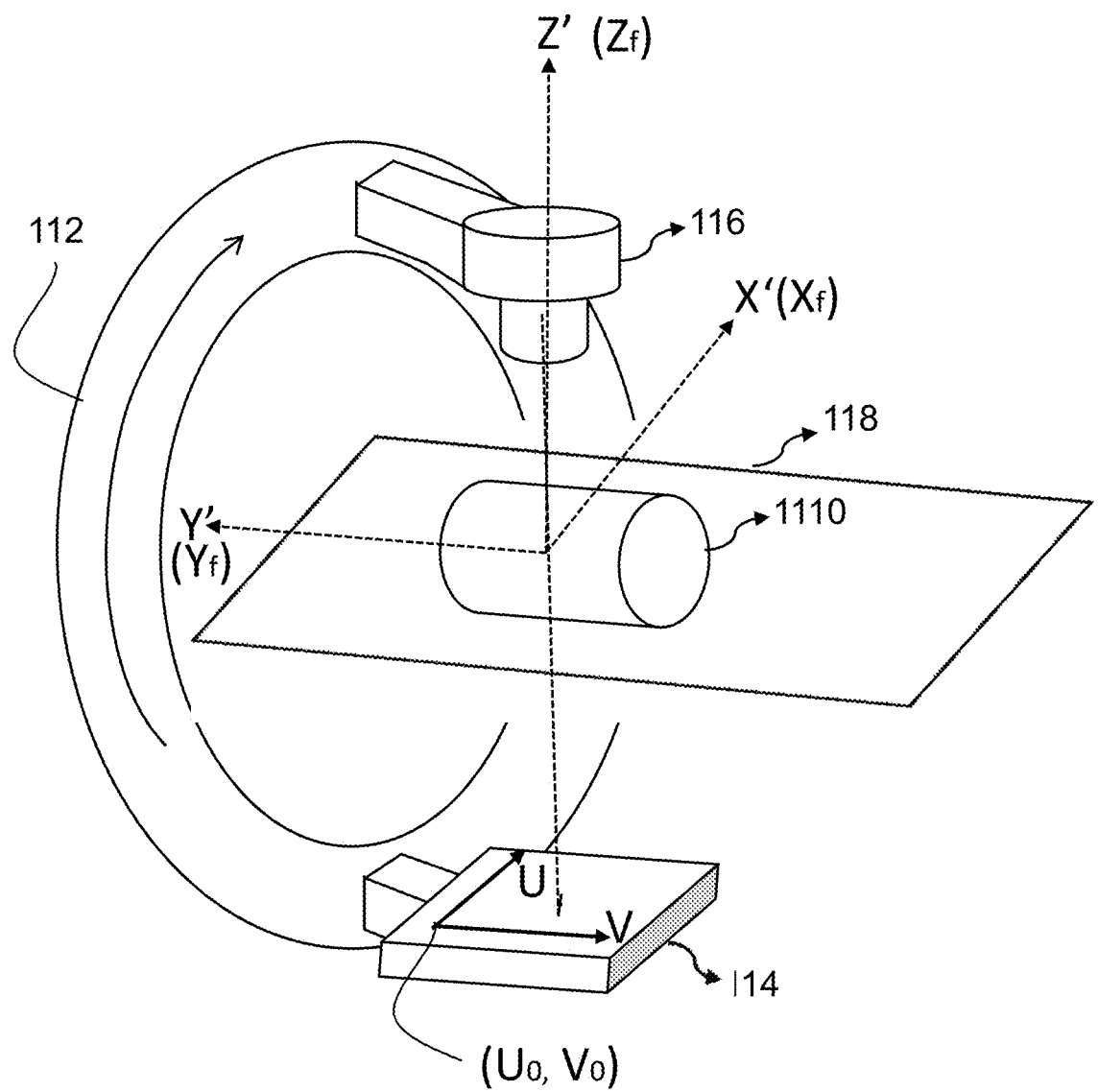
FIG. 11 is a schematic diagram illustrating an exemplary radiation device according to some embodiments of the present disclosure.

In some embodiments, the second image may include a projection image of a phantom. In some embodiments, the phantom may include a plurality of markers. In some embodiments, the marker may be made of a high density material. Exemplary materials suitable for a marker may include tungsten, steel, or the like, or a combination thereof. In some embodiments, the processing device 120 may obtain marker coordinates in a first coordinate system of the plurality of markers of the phantom. As used herein, the first coordinate system may also be referred to as a coordinate system of the phantom, or a phantom coordinate system. The origin of the first coordinate system may align with a specific point of the phantom. Merely by way of example, the origin of the first coordinate system may align with the center point of the phantom. In some embodiments, the first coordinate system may be a three-dimensional coordinate system (e.g., a Cartesian coordinate system). Merely by way of example, as illustrated in FIG. 11, the first coordinate system may include a first axis (e.g., Y' axis), a second axis perpendicular to the first axis (e.g., X' axis), and a third axis perpendicular to the first axis and the second axis (e.g., Z' axis). Specifically, the X' axis and the Z' axis may be in a vertical plane, the X' axis and the Y' axis may be in a horizontal plane, and the Y' axis may be along with the center axis of the phantom.

The position of the plurality of markers of the phantom may be registered with the first coordinate system. For example, the plurality of markers of the phantom may be assigned with one or more coordinates in the first coordinate system, based on the position of the plurality of markers of the phantom with respect to the origin of the first coordinate system (e.g., the center point of the phantom). The coordinates assigned to the plurality of markers may also be referred to as marker coordinates of the plurality of markers in the first coordinate system.

The projection data relating to the phantom may be assigned one or more coordinates in a third coordinate system relating to the detector 114 of the imaging device, based on the position of the projection data (e.g., its corresponding position on the detector 114) with respect to the origin of the third coordinate system (e.g., a certain position on the detector 114). The coordinates assigned to the projection data relating to the plurality of markers of the phantom may also be referred to as a projection coordinate of the plurality of markers (of the phantom) in the third coordinate system. As used herein, the third coordinate system may also be referred to as an image coordinate system of the radiation system 100. The origin of the third coordinate system may correspond to a point in the detector 114. The point may be, for example, a center point of the detector 114, a top left corner point of the detector 114, a top right corner point of the detector 114, etc. The third coordinate system may be two dimensional or three dimensional. Merely by way of example, as illustrated in FIG. 11, the third coordinate system may be a two dimensional coordinate system defined by a U axis and a V axis. The U axis and the V axis may be parallel to the X' axis and the Y' axis, respectively.

The processing device 120 may determine a plurality of projection matrices of the first coordinate system based on the coordinates of the plurality of markers in the first coordinate system and the projection coordinates of the plurality of markers in the third coordinate system. Merely by way of example, for a gantry angle, the projection matrix of the first coordinate system corresponding to the gantry angle may be determined by Equation (1):

$$t_i \begin{bmatrix} u_i \\ v_i \\ 1 \end{bmatrix} = \begin{bmatrix} p_{11}x_i + p_{12}x_i + p_{13}z_i + p_{14} \\ p_{21}x_i + p_{22}x_i + p_{23}z_i + p_{24} \\ p_{31}x_i + p_{32}x_i + p_{33}z_i + p_{34} \end{bmatrix}, \quad (1)$$

where $(x_i, y_i, z_i)$ refers to coordinates of the ith marker in the first coordinate system; $(u_i, v_i)$ refers to projection coordinates of the ith marker in the third coordinate system; index i refers to an integer larger than 1; and $t_i$ refers to a weight factor. Merely by way of example, the weight factor may relate to a penetration length of an X-ray emitted by the radiation source within the phantom.

The projection matrix of the first coordinate system may be further expressed as Equation (2):

$$P = \begin{bmatrix} p_{11} & p_{12} & p_{13} & p_{14} \\ p_{21} & p_{22} & p_{23} & p_{24} \\ p_{31} & p_{32} & p_{33} & p_{34} \end{bmatrix}, \qquad (2)$$

where P refers to a projection matrix of the first coordinate system; and each of $p_{11}$ through $p_{34}$ refers to an element of the projection matrix.

In some embodiments, the plurality of projection matrices of the first coordinate system may include a first projection matrix corresponding to a first gantry angle, a second projection matrix corresponding to a second gantry angle, a third projection matrix corresponding to a third gantry angle, . . . , and a n-th projection matrix corresponding to a n-th gantry angle.

The processing device 120 may determine a transformation matrix between the first coordinate system and a second coordinate system based on at least some of the projection matrices of the first coordinate system and the corresponding gantry angles. As used herein, the second coordinate system may also be referred to as a coordinate system of the radiation system 100. The origin of the second coordinate system may align with the intersection of the rotation plane of the radiation source and the rotation axis. In some embodiments, the second coordinate system may be an International Electrotechnical Commission (IEC) fixed coordinate system. The IEC fixed coordinate system may be a three-dimensional coordinate system. The IEC fixed coordinate system may include an $X_f$ axis (i.e., the X axis illustrated in FIG. 1), a $Y_f$ axis (i.e., the Y axis illustrated in FIG. 1), and a $Z_f$ axis (i.e., the Z axis illustrated in FIG. 1). The $X_f$ axis, the $Y_f$ axis, and the $Z_f$ axis may be defined according to the rotation plane and/or the rotation axis of the radiation source. The rotation axis of the radiation source is normal to the rotation plane. Specifically, the rotation axis of the radiation source may be defined as $Y_f$ axis. The $X_f$ axis and the $Z_f$ axis may be in the rotation plane of the radiation source. Specifically, the $Z_f$ axis may point from the center of the radiation system 100 (or the origin of the second coordinate system) to the radiation source, when the gantry angle is 0 degrees. The $X_f$ axis may be determined according to the right handed coordinate system including the $Z_f$ axis, the $Y_f$ axis, as illustrated in FIG. 11.

In some embodiments, the processing device 120 may determine the coordinates of the origin (or referred to as the origin coordinate) of the second coordinate system in the first coordinate system and a rotation angle of the second coordinate system from the first coordinate system based on the plurality of projection matrices of the first coordinate system and the plurality of gantry angles. The processing device 120 may determine the transformation matrix between the first coordinate system and the second coordinate system based on the determined origin coordinate and the rotation angle of the second coordinate system. Merely by way of example, the transformation matrix may be expressed as Equation (3):

$$T_{trans} = \begin{bmatrix} n_{x1} & n_{y1} & n_{z1} & -x_0 \\ n_{x2} & n_{y2} & n_{z2} & -y_0 \\ n_{x3} & n_{y3} & n_{z3} & -z_0 \end{bmatrix}, \qquad (3)$$

where $(x_0, y_0, z_0)$ refers to an origin coordinate of the second coordinate system in the first coordinate system; $(n_{x1}, n_{x2}, n_{x3})$ refers to a first unit vector along the $X_f$ axis of the second coordinate system in the first coordinate system; $(n_{y1}, n_{y2}, n_{y3})$ refers to a second unit vector along the $Y_f$ axis of the second coordinate system in the first coordinate system; $(n_{z1}, n_{z2}, n_{z3})$ refers to a third unit vector along the $Z_f$ axis of the second coordinate system in the first coordinate system; and $T_{trans}$ refers to a transformation matrix configured to, for example, transform position information expressed in terms of the first coordinate system to information expressed in terms of the second coordinate system.

The processing device 120 may determine a plurality of projection matrices of the second coordinate system based on the plurality of projection matrices of the first coordinate system and the transformation matrix. A projection matrix of the second coordinate system may be determined based on a corresponding projection matrix of the first coordinate system and the determined transformation matrix. A projection matrix of the second coordinate system is considered corresponding to a projection matrix of the first coordinate system when they both correspond to a same gantry angle. Merely by way of example, the projection matrix of the second coordinate system may be determined by Equation (4):

$$P_{IEC} = P \times T_{trans}, \qquad (4)$$

where $P_{IEC}$ refers to a projection matrix of the second coordinate system.

The processing device 120 may determine the second projection position of the second axis of a radiation beam on the imaging device based on the plurality of projection matrices of the second coordinate system. Merely by way of example, a plurality of projection matrices of the second coordinate system may be determined based on the projection data of the phantom and coordinates of a plurality of markers of the phantom in the first coordinate system. Further, the projection coordinate of a source $(u_0, v_0)$ (as illustrated in FIG. 11) in the third coordinate system may be determined based on the plurality of projection matrices of the second coordinate system. The second projection position of the second axis of the radiation beam on the imaging device may be coordinates of a detector unit on which the second axis of the radiation beam impinged on.

More descriptions for determining the projection position of the second axis of the radiation beam on the imaging device may be found in, e.g., Chinese Application No. CN201710640498.1 filed on Jul. 31, 2017, the contents of which are hereby incorporated by reference.

In 830, the processing device 120 (e.g., the offset determination module 620) may determine, based on the first projection position of the first axis of the collimator on the imaging device and the second projection position of the second axis of the radiation beam on the imaging device, an offset distance associated with the SID.

In some embodiments, the processing device 120 may determine a distance between the first projection position of the first axis of the collimator on the imaging device and the second projection position of the second axis of the radiation beam on the imaging device on an XOZ plane or a YOZ plane as the offset distance associated with the SID. For example, assuming that the first projection position of the first axis of the collimator on the imaging device is (u, v), and the second projection position of the second axis of the radiation beam on the imaging device is (u', v'), the processing device 120 may determine that the offset distance associated with the SID on the XOZ plane is $\Delta u = u' - u$, and the offset distance associated with the SID on the YOZ plane is $\Delta v = v' - v$.

In some embodiments, the processing device 120 may determine a distance between the first projection position of the first axis of the collimator on the imaging device and the second projection position of the second axis of the radiation beam on the imaging device as the offset distance associated with the SID. For example, assuming that the first projection position of the first axis of the collimator on the imaging device is (u, v), and the second projection position of the second axis of the radiation beam on the imaging device is (u', v'), the processing device 120 may determine that the offset distance associated with the SID is $d=\sqrt{(\Delta u)^2+(\Delta v)^2}$.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 9:
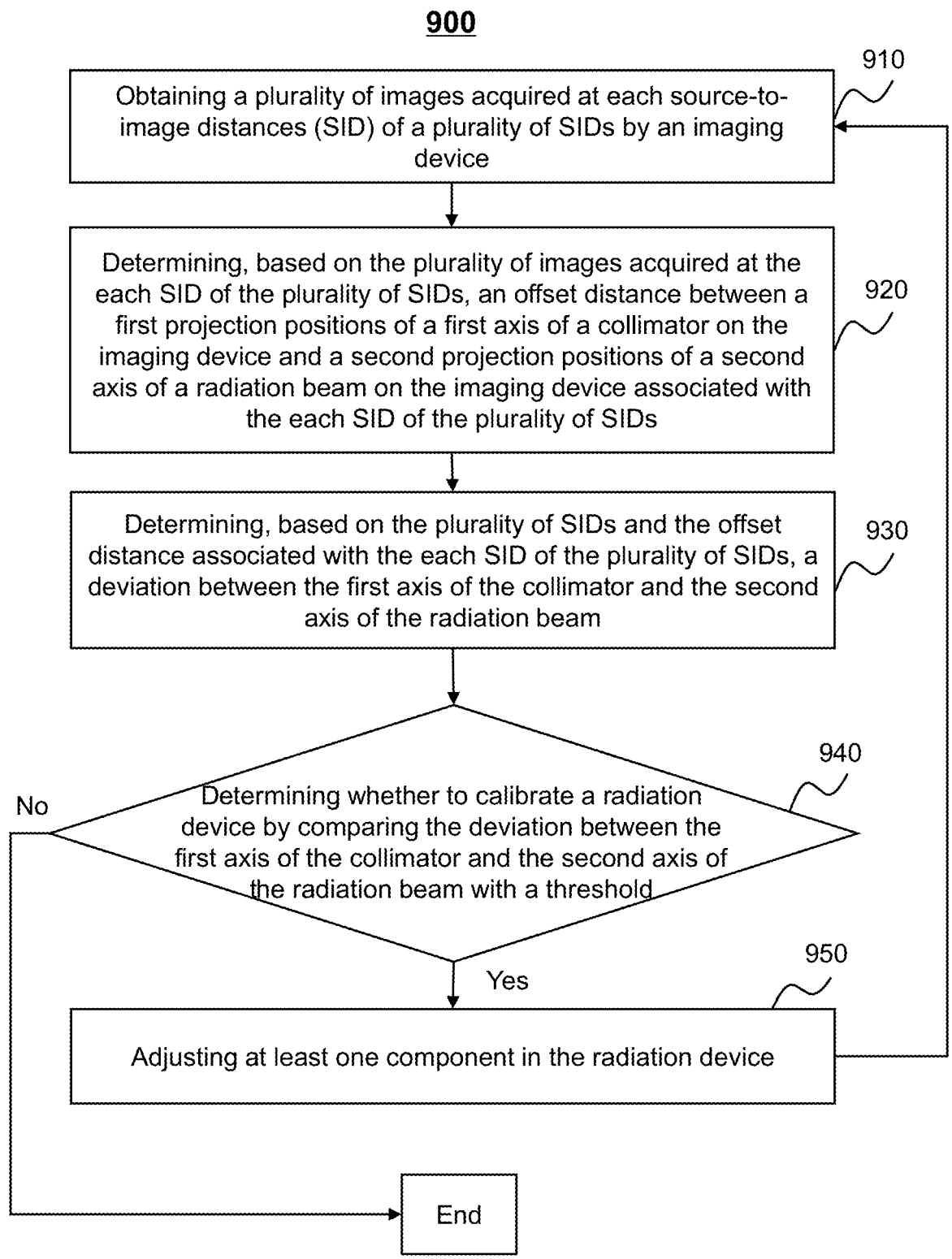
FIG. 9 is a flowchart illustrating an exemplary process for calibrating a radiation device according to some embodiments of the present disclosure.

FIG. 9 is a flowchart illustrating an exemplary process for calibrating a radiation device according to some embodiments of the present disclosure. In some embodiments, the process 900 may be implemented in the radiation system 100 illustrated in FIG. 1. For example, the process 900 may be stored in the storage device 130 and/or the storage (e.g., the storage 420, the storage 590) as a form of instructions, and invoked and/or executed by the processing device 120 (e.g., the processor 410 of the computing device 400 as illustrated in FIG. 4, the CPU 540 of the mobile device 500 as illustrated in FIG. 5). The operations of the illustrated process presented below are intended to be illustrative. In some embodiments, the process 900 may be accomplished with one or more additional operations not described, and/or without one or more of the operations discussed. Additionally, the order in which the operations of the process 900 as illustrated in FIG. 9 and described below is not intended to be limiting.

In 910, the processing device 120 (e.g., the obtaining module 610) may obtain a plurality of images acquired at each SID a plurality of SIDs by an imaging device.

In some embodiments, at each SID of the plurality of SIDs, the imaging device may generate one or more first images and one or more second images. More descriptions of the first image and the second image may be found elsewhere in the present disclosure (e.g., operation 710 in FIG. 7, and descriptions thereof).

In some embodiments, the processing device 120 may obtain the plurality of images (e.g., a first image, a second image) from the imaging device periodically (e.g., per second, per 2 seconds, per 5 seconds, per 10 seconds) or in real time. In some embodiments, the imaging device may transmit the plurality of images to a storage device (e.g., the storage device 130) periodically (e.g., per second, per 2 seconds, per 5 seconds, per 10 seconds) or in real time via the network 150. Further, the processing device 120 may access the storage device and retrieve the plurality of images.

In 920, the processing device 120 (e.g., the offset determination module 620) may determine, based on the plurality of images acquired at the each SID of the plurality of SIDs, an offset distance between a first projection position of a first axis of a collimator on the imaging device and a second projection position of a second axis of a radiation beam on the imaging device associated with the each SID of the plurality of SIDs.

In some embodiments, at each SID of the plurality of SIDs, the processing device 120 may determine the first projection position of the first axis of the collimator on the imaging device based on the at least one first image acquired at the SID. The processing device 120 may determine the second projection position of the second axis of the radiation beam on the imaging device based on the at least one second image acquired at the SID. The processing device 120 may determine an offset distance associated with the SID based on the first projection position of the first axis of the collimator on the imaging device and the second projection position of the second axis of the radiation beam on the imaging device. More descriptions of the determination of the offset distance may be found elsewhere in the present disclosure (e.g., FIG. 8, and descriptions thereof).

In 930, the processing device 120 (e.g., the deviation determination module 630) may determine, based on the plurality of SIDs and the offset distance associated with the each SID of the plurality of SIDs, a deviation between the first axis of the collimator and the second axis of the radiation beam.

In some embodiments, the deviation between the first axis of the collimator and the second axis of the radiation beam may include an angle of inclination of the first axis of the collimator relative to the second axis of the radiation beam, an offset of the first axis of the collimator relative to the second axis of the radiation beam, or the like, or any combination thereof. The offset of the first axis of the collimator relative to the second axis of the radiation beam may include an offset distance between the first projection position of the first axis of the collimator and the second projection position of the second axis of the radiation beam on a target plane of the imaging device.

In some embodiments, the processing device 120 may determine the angle of inclination of the first axis of the collimator relative to the second axis of the radiation beam and the offset of the first axis of the collimator relative to the second axis of the radiation beam based on the plurality of SIDs and the plurality of offset distances using a geometric relationship between the plurality of SIDs and the plurality of offset distances. More descriptions of the determination of the angle of inclination of the first axis of the collimator relative to the second axis of the radiation beam and the offset of the first axis of the collimator relative to the second axis of the radiation beam may be found elsewhere in the present disclosure (e.g., FIGS. 10, 12, 13, and descriptions thereof).

In some embodiments, the processing device 120 may determine, a plurality of initial angles of inclination of the first axis of the collimator relative to the second axis of the radiation beam and a plurality of initial offsets of the first axis of the collimator relative to the second axis of the radiation beam, based on the plurality SIDs and the plurality of offset distances, using a geometric relationship between the plurality of SIDs and the plurality of offset distances. The processing device 120 may determine a target angle of inclination of the first axis of the collimator relative to the second axis of the radiation beam and a target offset of the first axis of the collimator relative to the second axis of the radiation beam, based on the plurality of initial angles of inclination of the first axis of the collimator relative to the second axis of the radiation beam and the plurality of initial offsets of the first axis of the collimator relative to the second axis of the radiation beam. For example, the processing device 120 may determine an average value of the plurality of initial angles of inclination of the first axis of the collimator relative to the second axis of the radiation beam as the target angle of inclination of the first axis of the collimator relative to the second axis of the radiation beam.

The processing device 120 may determine an average value of the plurality of initial offsets of the first axis of the collimator relative to the second axis of the radiation beam as the target offset of the first axis of the collimator relative to the second axis of the radiation beam.

As another example, the processing device 120 may determine the target angle of inclination of the first axis of the collimator relative to the second axis of the radiation beam and the target offset of the first axis of the collimator relative to the second axis of the radiation beam, based on the plurality of initial angles of inclination of the first axis of the collimator relative to the second axis of the radiation beam and the plurality of initial offsets of the first axis of the collimator relative to the second axis of the radiation beam, by performing a fitting operation. The processing device 120 may fit the plurality of initial angles of inclination of the first axis of the collimator relative to the second axis of the radiation beam (or the plurality of initial offsets of the first axis of the collimator relative to the second axis of the radiation beam) according to an interpolation technique (e.g., a Gaussian interpolation, a polynomial interpolation). The processing device 120 may determine a value corresponding to a peak of a fitting curve as the target angle of inclination of the first axis of the collimator relative to the second axis of the radiation beam (or the target offset of the first axis of the collimator relative to the second axis of the radiation beam).

In 940, the processing device 120 (e.g., the comparison module 640) may determine whether to calibrate a radiation device (e.g., the radiation device 110) by comparing the deviation between the first axis of the collimator and the second axis of the radiation beam with a threshold.

In some embodiments, the threshold may be a default parameter stored in a storage device (e.g., the storage device 130). Additionally or alternatively, the threshold may be set manually by a user of the radiation system 100, or determined by one or more components of the radiation system 100 according to different situations. In some embodiments, the processing device 120 may determine the threshold based on historical data associated with a plurality of historical treatment operations and/or a plurality of historical imaging operations. For example, the processing device 120 may determine a plurality of deviations between the first axis of the collimator and the second axis of the radiation beam in the plurality of historical treatment operations and/or the plurality of historical imaging operations that satisfy a treatment need and/or an imaging need. The processing device 120 may determine an average deviation of the plurality of deviations between the first axis of the collimator and the second axis of the radiation beam as the threshold.

In some embodiments, the processing device 120 may determine whether the deviation between the first axis of the collimator and the second axis of the radiation beam is less than the threshold. In response to a determination that the deviation exceeds the threshold, the processing device 120 may determine that the radiation device needs to be calibrated, process 900 may proceed to operation 950.

In 950, the processing device 120 (e.g., the adjusting module 650) may adjust at least one component in the radiation device (e.g., the radiation device 110).

For example, the processing device 120 may adjust a position of the at least one component (e.g., an acceleration tube, a target) in the radiation device. In some embodiments, the at least one component (e.g., an acceleration tube, a target) in the radiation device may be adjusted automatically by one or more components (e.g., the processing device 120, the terminal 140) of the radiation system 100, or adjusted manually by a user of the radiation system 100. After the position of the at least one component in the radiation device is adjusted, process 900 may return to operation 910. Operation 910 to operation 950 may be repeated until the processing device 120 determines that the deviation is less than the threshold.

In response to a determination that the deviation is less than the threshold, the processing device 120 may determine that the radiation device does not need to be calibrated, process 900 may end. The radiation device 110 may image and/or treat a subject. For example, the processing device 120 may send instructions that cause the treatment head 116 to emit the radiation beam to image and/or treat the subject. It should be noted that, in response to a determination that the deviation is equal to the threshold, the processing device 120 may either determine that the radiation device needs to be calibrated or determine that the radiation device does not need to be calibrated.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the processing device 120 may determine a plurality of initial first projection positions of the first axis of the collimator on the imaging device and a plurality of initial second projection positions of the second axis of the radiation beam on the imaging device based on the plurality of images acquired at the plurality of SIDs. The processing device 120 may determine a target first projection position of the first axis of the collimator on the imaging device and a target second projection position of the second axis of the radiation beam on the imaging device based on the plurality of initial first projection positions of the first axis of the collimator on the imaging device and the plurality of initial second projection positions of the second axis of the radiation beam on the imaging device by performing a fitting operation. The processing device 120 may determine an offset distance between the target first projection position of the first axis of the collimator on the imaging device and the target second projection position of the second axis of the radiation beam on the imaging device. The processing device 120 may determine whether to calibrate the radiation device by comparing the offset distance with a threshold as described elsewhere in the present disclosure.

Figure 10:
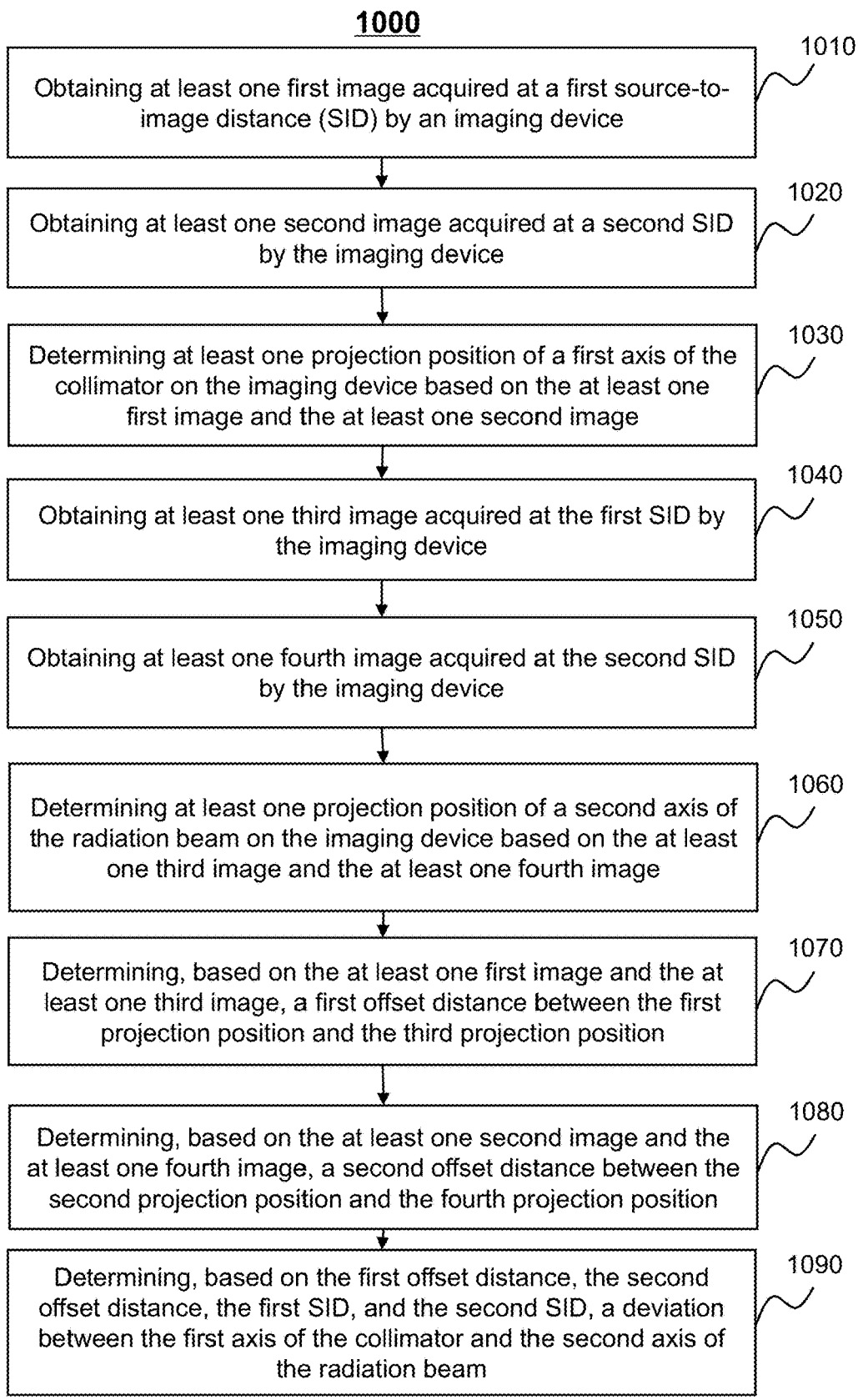
FIG. 10 is a flowchart illustrating an exemplary process for determining a deviation between a first axis of a collimator and a second axis of a radiation beam according to some embodiments of the present disclosure.

FIG. 10 is a flowchart illustrating an exemplary process for determining a deviation between a first axis of a collimator and a second axis of a radiation beam according to some embodiments of the present disclosure. In some embodiments, the process 1000 may be implemented in the radiation system 100 illustrated in FIG. 1. For example, the process 1000 may be stored in the storage device 130 and/or the storage (e.g., the storage 420, the storage 590) as a form of instructions, and invoked and/or executed by the processing device 120 (e.g., the processor 410 of the computing device 400 as illustrated in FIG. 4, the CPU 540 of the mobile device 500 as illustrated in FIG. 5). The operations of the illustrated process presented below are intended to be illustrative. In some embodiments, the process 1000 may be accomplished with one or more additional operations not described, and/or without one or more of the operations discussed. Additionally, the order in which the operations of the process 1000 as illustrated in FIG. 10 and described below is not intended to be limiting.

In 1010, the processing device 120 (e.g., the obtaining module 610) may obtain at least one first image acquired at a first source-to-image distance (SID) by an imaging device. In some embodiments, each of the at least one first image is used for determining a projection position of a first axis of the collimator on the imaging device. In some embodiments, the at least one first image may include a projection image of at least one of a marker board, a jaw, or a multi-leaf collimator. More descriptions of the first image may be found elsewhere in the present disclosure (e.g., operation 710 in FIG. 7, and descriptions thereof).

In 1020, the processing device 120 (e.g., the obtaining module 610) may obtain at least one second image acquired at a second SID acquired by the imaging device. The second SID may be different from the first SID. In some embodiments, each of the at least one second image is used for determining a projection position of a first axis of the collimator on the imaging device. In some embodiments, the at least one second image may include a projection image of at least one of a marker board, a jaw, or a multi-leaf collimator. More descriptions of the second image may be found elsewhere in the present disclosure (e.g., operation 710 in FIG. 7, and descriptions thereof).

In 1030, the processing device 120 (e.g., the offset determination module 620) may determine at least one projection position of a first axis of the collimator on the imaging device based on the at least one first image and the at least one second image.

The at least one projection position of the first axis of the collimator on the imaging device may include a first projection position of the first axis of the collimator on the imaging device when the imaging device is positioned to acquire the at least one first image at the first SID, and a second projection position of the first axis of the collimator on the imaging device when the imaging device is positioned to acquire the at least one second image at the second SID. More descriptions of the determination of the projection position may be found elsewhere in the present disclosure (e.g., operation 810 in FIG. 8, and descriptions thereof).

In 1040, the processing device 120 (e.g., the obtaining module 610) may obtain at least one third image acquired at the first SID acquired by the imaging device. In some embodiments, each of the at least one third image is used for determining a projection position of a second axis of the radiation beam on the imaging device. In some embodiments, the at least one third image may include a projection image of a phantom. More descriptions of the third image may be found elsewhere in the present disclosure (e.g., operation 710 in FIG. 7, and descriptions thereof).

In 1050, the processing device 120 (e.g., the obtaining module 610) may obtain at least one fourth image acquired at the second SID acquired by the imaging device. In some embodiments, each of the at least one fourth image is used for determining a projection position of a second axis of the radiation beam on the imaging device. In some embodiments, the at least one fourth image may include a projection image of a phantom. More descriptions of the fourth image may be found elsewhere in the present disclosure (e.g., operation 710 in FIG. 7, and descriptions thereof).

In 1060, the processing device 120 (e.g., the offset determination module 620) may determine at least one projection position of a second axis of the radiation beam on the imaging device based on the at least one third image and the at least one fourth image.

The at least one projection position of the second axis of the radiation beam on the imaging device may include a third projection position of the second axis of the radiation beam on the imaging device when the imaging device is positioned to acquire the at least one third image at the first SID, and a fourth projection position of the second axis of the radiation beam on the imaging device when the imaging device is positioned to acquire the at least one fourth image at the second SID. More descriptions of the determination of the projection position may be found elsewhere in the present disclosure (e.g., operation 820 in FIG. 8, and descriptions thereof).

In 1070, the processing device 120 (e.g., the offset determination module 620) may determine, based on the at least one first image and the at least one third image, a first offset distance between the first projection position and the third projection position.

In some embodiments, the processing device 120 may determine the first projection position of the first axis of the collimator on the imaging device based on the at least one first image. The processing device 120 may determine the third projection position of the second axis of the radiation beam on the imaging device based on the at least one third image. The processing device 120 may determine the first offset distance associated with the first SID based on the first projection position of the first axis of the collimator on the imaging device and the third projection position of the second axis of the radiation beam on the imaging device. For example, assuming that the first projection position of the first axis of the collimator on the imaging device is $(u_1, v_1)$, and the third projection position of the second axis of the radiation beam on the imaging device is $(u'_1, v'_1)$, the processing device 120 may determine that the first offset distance associated with the first SID on an XOZ plane is $\Delta_{u1} = u'_1 - u_1$, and the first offset distance associated with the first SID on a YOZ plane is $\Delta_{v1} = v'_1 - v_1$.

In 1080, the processing device 120 (e.g., the offset determination module 620) may determine, based on the at least one second image and the at least one fourth image, a second offset distance between the second projection position and the fourth projection position.

In some embodiments, the processing device 120 may determine the second projection position of the first axis of the collimator on the imaging device based on the at least one second image. The processing device 120 may determine the fourth projection position of the second axis of the radiation beam on the imaging device based on the at least one fourth image. The processing device 120 may determine the second offset distance associated with the second SID based on the second projection position of the first axis of the collimator on the imaging device and the fourth projection position of the second axis of the radiation beam on the imaging device. For example, assuming that the second projection position of the first axis of the collimator on the imaging device is $(u_2, v_2)$, and the fourth projection position of the second axis of the radiation beam on the imaging device is $(u'_2, v'_2)$, the processing device 120 may determine that the second offset distance associated with the second SID on the XOZ plane is $\Delta u_2 = u'_2 - u_2$, and the second offset distance associated with the second SID on the YOZ plane is $\Delta v_2 = v'_2 - v_2$.

In 1090, the processing device 120 (e.g., the deviation determination module 630) may determine, based on the first offset distance, the second offset distance, the first SID, and the second SID, a deviation between the first axis of the collimator and the second axis of the radiation beam.

In some embodiments, the deviation between the first axis of the collimator and the second axis of the radiation beam may include an angle of inclination of the first axis of the collimator relative to the second axis of the radiation beam, an offset of the first axis of the collimator relative to the second axis of the radiation beam, or the like, or any combination thereof. The offset of the first axis of the collimator relative to the second axis of the radiation beam may include an offset distance between the first projection position of the first axis of the collimator and the second projection position of the second axis of the radiation beam on a target plane of the imaging device.

In some embodiments, the processing device 120 may determine the angle of inclination of the first axis of the collimator relative to the second axis of the radiation beam on the XOZ plane based on the first offset distance on the XOZ plane, the second offset distance on the XOZ plane, the first SID, and the second SID. For example, the processing device 120 may determine the angle of inclination of the first axis of the collimator relative to the second axis of the radiation beam on the XOZ plane according to Equation (5):

$$\alpha_{XOZ} = \arctan\left(\frac{\Delta u_2 - \Delta u_1}{d_2 - d_1}\right), \quad (5)$$

where $\alpha_{XOZ}$ refers to an angle of inclination of the first axis of the collimator relative to the second axis of the radiation beam on the XOZ plane; $\Delta u_1$ refers to a first offset distance associated with a first SID on the XOZ plane; $\Delta u_2$ refers to a second offset distance associated with a second SID on the XOZ plane; $d_1$ refers to the first SID; and $d_2$ refers to the second SID. The processing device 120 may determine the offset of the first axis of the collimator relative to the second axis of the radiation beam on the XOZ plane based on the first offset distance on the XOZ plane, the second offset distance on the XOZ plane, the first SID, and the second SID. For example, the processing device 120 may determine the offset distance between the first projection position of the first axis of the collimator and the second projection position of the second axis of the radiation beam on the target plane of the imaging device on the XOZ plane according to Equation (6):

$$\Delta_{XOZ} = d_{XOZ} \times \tan(\alpha_{XOZ}), \quad (6)$$

where $\Delta_{XOZ}$ refers to an offset distance between the first projection position of the first axis of the collimator and the second projection position of the second axis of the radiation beam on the target plane of the imaging device on the XOZ plane; $\Delta d_{XOZ}$ refers to a distance from an intersection of the first axis of the collimator and the second axis of the radiation beam to the target plane of the imaging device; and $\alpha_{XOZ}$ refers to an angle of inclination of the first axis of the collimator relative to the second axis of the radiation beam on the XOZ plane. The distance from the intersection of the first axis of the collimator and the second axis of the radiation beam to the target plane of the imaging device may be determined according to Equation (7):

$$\Delta d_{XOZ} = \frac{\Delta u_1 d_2 - \Delta u_2 d_a}{\Delta u_2 - \Delta u_1}, \quad (7)$$

where $\Delta d_{XOZ}$ refers to a distance from an intersection of the first axis of the collimator and the second axis of the radiation beam to the target plane of the imaging device; $\Delta u_1$ refers to a first offset distance associated with a first SID on the XOZ plane; $\Delta u_2$ refers to a second offset distance associated with a second SID on the XOZ plane; $d_1$ refers to the first SID; and $d_2$ refers to the second SID. In some embodiments, $\tan(\alpha_{XOZ})$ may be determined according to Equation (8):

$$\tan(\alpha_{XOZ}) = \frac{\Delta u_2}{d_2 + \Delta d_{XOZ}} = \frac{\Delta u_1}{d_1 + \Delta d_{XOZ}} = \frac{\Delta u_2 - \Delta u_1}{d_2 - d_1}, \quad (8)$$

where $\Delta d_{XOZ}$ refers to a distance from an intersection of the first axis of the collimator and the second axis of the radiation beam to the target plane of the imaging device; $\Delta u_1$ refers to a first offset distance associated with a first SID on the XOZ plane; $\Delta u_2$ refers to a second offset distance associated with a second SID on the XOZ plane; $d_1$ refers to the first SID; and $d_2$ refers to the second SID.

Similarly, the processing device 120 may determine the angle of inclination of the first axis of the collimator relative to the second axis of the radiation beam on the YOZ plane and the offset of the first axis of the collimator relative to the second axis of the radiation beam on the YOZ plane based on the first offset distance on the YOZ plane, the second offset distance on the YOZ distance, the first SID, and the second SID. For example, the processing device 120 may determine the angle of inclination of the first axis of the collimator relative to the second axis of the radiation beam on the YOZ plane and the offset of the first axis of the collimator relative to the second axis of the radiation beam on the YOZ plane by replacing $\Delta_{u1}$ and $\Delta u_2$ with $\Delta v_1$ and $\Delta v_2$ in Equations (5)~(8).

In some embodiments, the processing device 120 may determine the deviation between the first axis of the collimator and the second axis of the radiation beam based on a plurality of SIDs and a plurality of offset distances. For example, the angle of inclination of the first axis of the collimator relative to the second axis of the radiation beam on the XOZ plane and the offset of the first axis of the collimator relative to the second axis of the radiation beam on the XOZ plane may be determined according to Equation (9):

$$\tan\alpha_{XOZ} = \frac{\Delta u_1}{d_1 + \Delta d_{XOZ}} = \frac{\Delta u_2}{d_2 + \Delta d_{XOZ}} = \ldots = \frac{\Delta u_n}{d_n + \Delta d_{XOZ}}, \quad (9)$$

where $\alpha_{XOZ}$ refers to an angle of inclination of the first axis of the collimator relative to the second axis of the radiation beam on the XOZ plane; $\Delta d_{XOZ}$ refers to a distance from an intersection of the first axis of the collimator and the second axis of the radiation beam to the target plane of the imaging device; $\Delta u_i$ refers to the ith offset distance associated with the ith SID on the XOZ plane; $d_i$ refers to the ith SID; and i refers to an integer, i=1, 2, 3, . . . , n. Equation (9) may be expressed as Equations (10)~(12):

$$(d_1 + \Delta d_{XOZ})\tan\alpha_{XOZ} = \Delta u_1, \quad (10)$$

$$(d_2 + \Delta d_{XOZ})\tan\alpha_{XOZ} = \Delta u_2, \quad (11)$$

$$(d_n + \Delta d_{XOZ})\tan\alpha_{XOZ} = \Delta u_n, \quad (12)$$

Equations (10)~(12) may be expressed as Equation (13):

$$\begin{bmatrix} d_1 & 1 \\ d_2 & 1 \\ \ldots & 1 \\ d_n & 1 \end{bmatrix} \begin{bmatrix} \tan\alpha_{XOZ} \\ \Delta d_{XOZ}\tan\alpha_{XOZ} \end{bmatrix} = \begin{bmatrix} \Delta u_1 \\ \Delta u_2 \\ \ldots \\ \Delta u_n \end{bmatrix}. \quad (13)$$

Similarly, the processing device 120 may determine the angle of inclination of the first axis of the collimator relative to the second axis of the radiation beam on the YOZ plane and the offset of the first axis of the collimator relative to the second axis of the radiation beam on the YOZ plane based on the plurality of SIDs and the plurality of offset distances. For example, the processing device 120 may determine the angle of inclination of the first axis of the collimator relative to the second axis of the radiation beam on the YOZ plane and the offset of the first axis of the collimator relative to the second axis of the radiation beam on the YOZ plane by replacing $\Delta u_1$ and $\Delta u_2$ with $\Delta v_1$ and $\Delta v_2$ in Equations (9)~(13).

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be added or omitted. For example, an operation for determining whether to calibrate a radiation device (e.g., the radiation device 110) may be added after operation 1070. The processing device 120 may determine whether to calibrate the radiation device by comparing the deviation between the first axis of the collimator and the second axis of the radiation beam with a threshold as described in connection with operation 940. In response to a determination that the radiation device needs to be calibrated, the processing device 120 (e.g., the adjusting module 650) may adjust at least one component in the radiation device (e.g., the radiation device 110) as described in connection with operation 950. In some embodiments, two or more operations may be combined into a single operation. For example, operation 1010 and operation 1030 may be combined into a single operation. As another example, operation 1020 and operation 1040 may be combined into a single operation. In some embodiments, the order of operations in process 1000 may be changed. For example, operation 1030 may be performed before operation 1020.

FIG. 11 is a schematic diagram illustrating an exemplary radiation device according to some embodiments of the present disclosure. As illustrated in FIG. 11, the radiation device 110 may include the gantry 112, the detector 114, the treatment head 116 and the table 118 as described elsewhere in the present disclosure.

In some embodiments, a first coordinate system may be determined based on a phantom 1110. The origin of the first coordinate system may align with the center point of the phantom 1110. The first coordinate system may be defined by an X' axis, a Y' axis, and a Z' axis. Specifically, the X' axis and the Z' axis may be in a vertical plane, the X' axis and the Y' axis may be in a horizontal plane, the Y' axis may be along the center axis of the phantom 1110.

In some embodiments, a second coordinate system may be determined based on the radiation device 110. The origin of the second coordinate system may align with the intersection of the rotation plane and the rotation axis. The second coordinate system may be an International Electrotechnical Commission (IEC) fixed coordinate system. As illustrated in FIG. 11, the second coordinate system may include an $X_f$ axis (i.e., the X axis illustrated in FIG. 1), a $Y_f$ axis (i.e., the Y axis illustrated in FIG. 1), and a $Z_f$ axis (i.e., the Z axis illustrated in FIG. 1). The rotation axis of the treatment head 116 may be coincide with the $Y_f$ axis. The $X_f$ axis and the $Z_f$ axis may be in a vertical plane, the $X_f$ axis and the $Y_f$ axis may be in a horizontal plane. The positive $Z_f$ axis may point from the center of the radiation device 110 (or the origin of the second coordinate system) to the treatment head 116, when the gantry angle is 0 degree. The $X_f$ axis may be determined according to the right handed coordinate system including the $Z_f$ axis, the $Y_f$ axis. In an ideal scenario, the second coordinate system may align with the first coordinate system as illustrated in FIG. 11, and the origin of the second coordinate system may coincide with the origin of the first coordinate system.

In some embodiments, a third coordinate system related to the detector 114 may be determined. The origin may be, for example, a top left corner point of the detector 114 viewed from the direction facing the gantry. The third coordinate system may be a two dimensional coordinate system defined by a U axis and a V axis. For instance, the U axis and the V axis may be parallel to the Xf axis and the inversely Yf axis of the second coordinate system, respectively.

Figure 12:
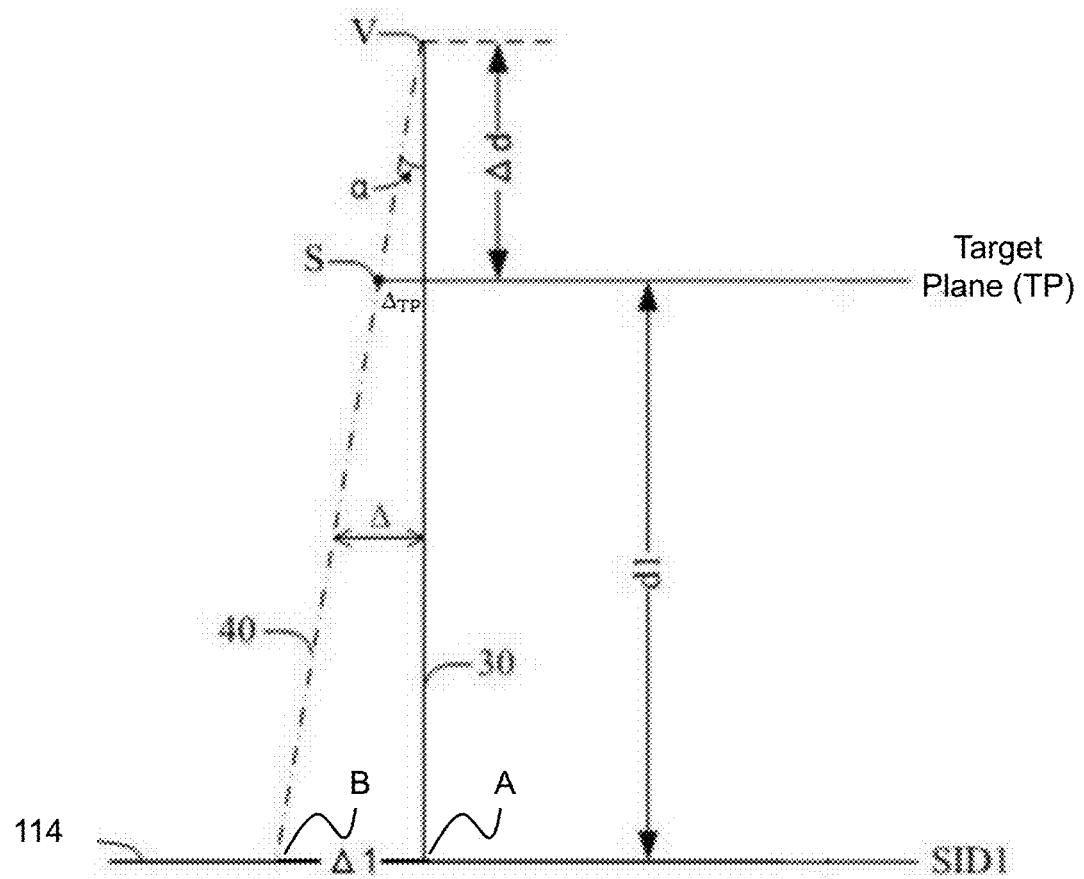
FIG. 12 is a schematic diagram illustrating an exemplary first projection position of a first axis of a collimator on an imaging device and an exemplary second projection position of a second axis of a radiation beam on the imaging device according to some embodiments of the present disclosure.
Figure 13:
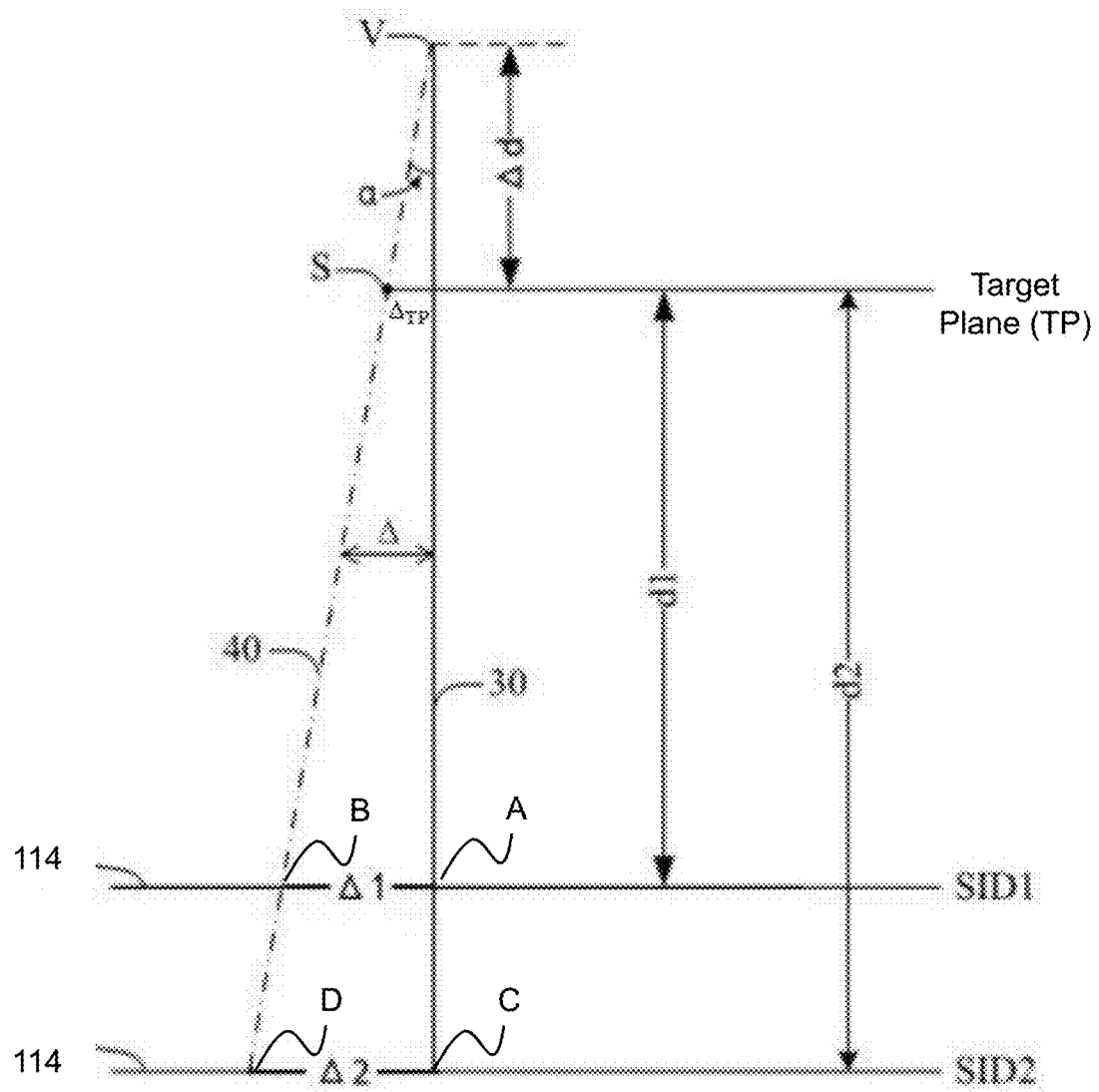
FIG. 13 is a schematic diagram illustrating exemplary first projection positions of a first axis of a collimator on an imaging device and exemplary second projection positions of a second axis of a radiation beam on the imaging device according to some embodiments of the present disclosure.

FIGS. 12 and 13 are schematic diagrams illustrating exemplary first projection positions of a first axis of a collimator on an imaging device and exemplary second projection positions of a second axis of a radiation beam on the imaging device according to some embodiments of the present disclosure.

As illustrated in FIGS. 12 and 13, a radiation source in a treatment head (e.g., the treatment head 116) may be located at a point S on a target plane (TP) of an imaging device to emit a radiation beam. The radiation beam may have a beam axis 40 (also referred to as a second axis 40). A collimator (e.g., the collimator 31) in the treatment head may rotated around a first axis 30. A point V may refer to an intersection of the first axis 30 and the second axis 40. An angle α may refer to an angle of inclination of the first axis 30 of the collimator relative to the second axis 40 of the radiation beam. An offset Δ may refer to an offset of the first axis 30 of the collimator relative to the second axis 40 of the radiation beam. An offset distance ΔTP may refer to an offset distance between the first projection position of the first axis 30 of the collimator and a second projection position of the second axis 40 of the radiation beam on a target plane (TP) of the imaging device. Ad may refer to a distance from the intersection (i.e., the point V) of the first axis 30 and the second axis 40 to the target plane of the imaging device.

A first projection position (i.e., a point A) of the first axis 30 of the collimator on the detector (e.g., the detector 114) of the imaging device may be determined based on at least one first image acquired at an SID1 (i.e., d1) as described in connection with operation 810. A first projection position (i.e., a point B) of the second axis 40 of the radiation beam on the detector (e.g., the detector 114) of the imaging device may be determined based on at least one second image acquired at the SID1 as described in connection with operation 820. A first offset distance (i.e., Δ1) between the first projection position (i.e., the point A) of the first axis 30 of the collimator on the detector 114 and the first projection position (i.e., the point B) of the second axis 40 of the radiation beam on the detector 114 may be determined based on the first projection position (i.e., the point A) of the first axis 30 of the collimator on the detector 114 and the first projection position (i.e., the point B) of the second axis 40 of the radiation beam on the detector 114 as described in connection with operation 830.

In some embodiments, as illustrated in FIG. 13, a second projection position (i.e., a point C) of the first axis 30 of the collimator on the detector (e.g., the detector 114) may be determined based on at least one first image acquired at an SID2 (i.e., d2) as described in connection with operation 810. A second projection position (i.e., a point D) of the second axis 40 of the radiation beam on the detector (e.g., the detector 114) may be determined based on at least one second image acquired at the SID2 as described in connection with operation 820. A second offset distance (i.e., Δ2) between the second projection position (i.e., the point C) of the first axis 30 of the collimator on the detector 114 and the second projection position (i.e., the point D) of the second axis 40 of the radiation beam on the detector 114 may be determined based on the second projection position (i.e., the point C) of the first axis 30 of the collimator on the detector 114 and the second projection position (i.e., the point D) of the second axis 40 of the radiation beam on the detector 114 as described in connection with operation 830.

In some embodiments, a deviation between the first axis 30 of the collimator and the second axis 40 of the radiation beam (e.g., the angle α, the offset distance ΔTP) may be determined based on the first offset distance (i.e., Δ1), the second offset distance (i.e., Δ2), the SID1 (i.e., d1), and the SID2 (i.e., d2), as described in connection with operation 1070.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "module," "unit," "component," "device," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claim subject matter lie in less than all features of a single foregoing disclosed embodiment.

I claim:

1. A method for calibrating a radiation device implemented on a computing device having one or more processors and one or more storage devices, the radiation device includes a radiation source, a collimator, and a detector of an imaging device disposed opposite to the radiation source, the radiation source being configured to emit a radiation beam, the collimator being configured to block the radiation beam, the method comprising:
   obtaining a plurality of images acquired at a source-to-image distance (SID) by the imaging device, wherein the plurality of images include at least one first image and at least one second image, the at least one first image is obtained by rotating the collimator around a first axis of the collimator, and the at least one second image is obtained by imaging a phantom from at least one gantry angle;
   determining, based on the at least one first image, a first projection position of the first axis of the collimator on the imaging device;
   determining, based on the at least one second image, a second projection position of a second axis of the radiation beam on the imaging device;
   determining, based on the first projection position and the second projection position, an offset distance between the first projection position and the second projection position; and
   determining whether to calibrate the radiation device by comparing the offset distance with a threshold.

2. The method of claim 1, wherein determining whether to calibrate the radiation device by comparing the offset distance with a threshold comprises determining that the offset distance exceeds the threshold, and the method further comprising:
   calibrating the radiation device by adjusting at least one component of the radiation device.

3. The method of claim 1, wherein the at least one first image includes a projection image of at least one of a marker board, a jaw, or a multi-leaf collimator.

4. The method of claim 1, wherein the at least one second image includes a projection image of the phantom.

5. The method of claim 1, wherein the imaging device is an electronic portal imaging device (EPID).

6. A method for calibrating a radiation device implemented on a computing device having one or more processors and one or more storage devices, the radiation device includes a radiation source, a collimator, and a detector of an imaging device disposed opposite to the radiation source, the radiation source being configured to emit a radiation beam, the collimator being configured to block the radiation beam, the method comprising:
   obtaining a plurality of images acquired at each source-to-image distances (SID) of a plurality of SIDs by the imaging device, wherein the plurality of images include at least one first image and at least one second image, the at least one first image is obtained by rotating the collimator around the first axis of the collimator, and the at least one second image is obtained by imaging a phantom from at least one gantry angle;
   determining, based on the at least one first image, a first projection position of a first axis of the collimator on the imaging device associated with the each SID of the plurality of SIDs;
   determining, based on the at least one second image, a second projection position of a second axis of the radiation beam on the imaging device associated with the each SID of the plurality of SIDs;
   determining, based on the first projection position of the first axis of the collimator on the imaging device associated with the each SID of the plurality of SIDs and the second projection position of the second axis of the radiation beam on the imaging device associated with the each SID of the plurality of SIDs, an offset distance associated with the each SID of the plurality of SIDs; and
   determining, based on the plurality of SIDs and the offset distance associated with the each SID of the plurality of SIDs, a deviation between the first axis of the collimator and the second axis of the radiation beam.

7. The method of claim 6, wherein the at least one first image includes a projection image of at least one of a marker board, a jaw, or a multi-leaf collimator.

8. The method of claim 6, wherein the at least one second image includes a projection image of a phantom.

9. The method of claim 6, wherein the deviation between the first axis of the collimator and the second axis of the radiation beam includes at least one of
   an angle of inclination of the first axis of the collimator relative to the second axis of the radiation beam, or
   an offset of the first axis of the collimator relative to the second axis of the radiation beam.

10. The method of claim 9, wherein the offset of the first axis of the collimator relative to the second axis of the radiation beam includes an offset distance between a first projection position of the first axis of the collimator and a second projection position of the second axis of the radiation beam on a target plane of the imaging device.

11. The method of claim 9, wherein determining, based on the plurality of SIDs and the plurality of offset distances, the deviation between the first axis of the collimator and the second axis of the radiation beam comprises:
   determining, based on the plurality of SIDs, the plurality of offset distances, and a geometric relationship between the plurality of SIDs and the plurality of offset distances, at least one of an angle of inclination of the first axis of the collimator relative to the second axis of the radiation beam or an offset of the first axis of the collimator relative to the second axis of the radiation beam.

12. The method of claim 9, wherein determining, based on the plurality of SIDs and the plurality of offset distances, the deviation between the first axis of the collimator and the second axis of the radiation beam comprises:
   determining, based on the plurality SIDs, the plurality of offset distances, and a geometric relationship between the plurality of SIDs and the plurality of offset distances, at least one of a plurality of initial angles of inclination of the first axis of the collimator relative to the second axis of the radiation beam or a plurality of initial offsets of the first axis of the collimator relative to the second axis of the radiation beam; and
   determining, by performing a fitting operation based on at least one of the plurality of initial angles of inclination of the first axis of the collimator relative to the second axis of the radiation beam or the plurality of initial offsets of the first axis of the collimator relative to the second axis of the radiation beam, at least one of a target angle of inclination of the first axis of the collimator relative to the second axis of the radiation beam or a target offset of the first axis of the collimator relative to the second axis of the radiation beam.

13. The method of claim 6, further comprising:
determining whether to calibrate the radiation device by comparing the deviation between the first axis of the collimator and the second axis of the radiation beam with a threshold.

14. The method of claim 13, wherein determining whether to calibrate the radiation device by comparing the deviation between the first axis of the collimator and the second axis of the radiation beam with a threshold comprises determining that the deviation exceeds the threshold, and the method further comprising:
calibrating the radiation device by adjusting at least one component of the radiation device.

15. The method of claim 6, wherein the imaging device is an electronic portal imaging device (EPID).

16. A method for calibrating a radiation device implemented on a computing device having one or more processors and one or more storage devices, the radiation device includes a radiation source, a collimator, and a detector of an imaging device disposed opposite to the radiation source, the radiation source being configured to emit a radiation beam, the collimator being configured to block the radiation beam, the method comprising:
obtaining at least one first image acquired at a first source-to-image distance (SID) by the imaging device;
obtaining at least one second image acquired at a second SID by the imaging device, wherein the at least one first image and the at least one second image are obtained by rotating the collimator around the first axis of the collimator;
determining at least one projection position of a first axis of the collimator on the imaging device based on the at least one first image and the at least one second image, the at least one projection position of the first axis of the collimator on the imaging device includes a first projection position of the first axis of the collimator on the imaging device when the imaging device is positioned to acquire the at least one first image at the first SID, and a second projection position of the first axis of the collimator on the imaging device when the imaging device is positioned to acquire the at least one second image at the second SID;
obtaining at least one third image acquired at the first SID by the imaging device;
obtaining at least one fourth image acquired at the second SID by the imaging device, wherein the at least one third image and the at least one fourth image are obtained by imaging a phantom from at least one gantry angle;
determining at least one projection position of a second axis of the radiation beam on the imaging device based on the at least one third image and the at least one fourth image, the at least one projection position of the second axis of the radiation beam on the imaging device includes a third projection position of the second axis of the radiation beam on the imaging device when the imaging device is positioned to acquire the at least one third image at the first SID, and a fourth projection position of the second axis of the radiation beam on the imaging device when the imaging device is positioned to acquire the at least one fourth image at the second SID;
determining, based on the at least one first image and the at least one third image, a first offset distance between the first projection position and the third projection position;
determining, based on the at least one second image and the at least one fourth image, a second offset distance between the second projection position and the fourth projection position; and
determining, based on the first offset distance, the second offset distance, the first SID, and the second SID, a deviation between the first axis of the collimator and the second axis of the radiation beam.

17. The method of claim 3, wherein a rotation center of the at least one of the marker board, the jaw, or the multi-leaf collimator in the at least one first image is determined as the first projection position of the first axis of the collimator on the imaging device.

18. The method of claim 1, wherein the phantom includes a plurality of markers, and the determining, based on the at least one second image, a second projection position of a second axis of the radiation beam on the imaging device associated with the each SID of the plurality of SIDs comprises:
obtaining marker coordinates in a phantom coordinate system of the plurality of markers of the phantom;
obtaining projection coordinates of the plurality of markers in an image coordinate system;
determining a plurality of projection matrices of the phantom coordinate system based on the marker coordinates of the plurality of markers in the phantom coordinate system and the projection coordinates of the plurality of markers in the image coordinate system;
determining a transformation matrix between the phantom coordinate system and a coordinate system of a radiation system based on at least some of the plurality of projection matrices of the phantom coordinate system;
determining a plurality of projection matrices of the coordinate system of the radiation system based on the plurality of projection matrices of the phantom coordinate system and the transformation matrix; and
determining the second projection position of the second axis of the radiation beam on the imaging device based on the plurality of projection matrices of the coordinate system of the radiation system.

* * * * *